United States Patent
Laufer et al.

(10) Patent No.: US 6,878,738 B1
(45) Date of Patent: Apr. 12, 2005

(54) ANTI-INFLAMMATORY OXO DERIVATIVES AND HYDROXY DERIVATIVES OF PYRROLIZINES, AND THEIR PHARMACEUTICAL USE

(75) Inventors: Stefan Laufer, Blaubeuren (DE); Karola Tollmann, Brechen (DE); Hans-Guenter Striegel, Blaustein (DE)

(73) Assignee: Merckle GmbH, Ulm (DE)

( * ) Notice: Subject to any disclaimer, the term of this patent is extended or adjusted under 35 U.S.C. 154(b) by 0 days.

(21) Appl. No.: 10/129,102

(22) PCT Filed: Nov. 23, 1999

(86) PCT No.: PCT/EP99/09057

§ 371 (c)(1), (2), (4) Date: Sep. 9, 2002

(87) PCT Pub. No.: WO01/05792

PCT Pub. Date: Jan. 25, 2001

(51) Int. Cl.$^7$ .................. A61K 31/40; C07D 209/52
(52) U.S. Cl. .................. 514/413; 548/512; 548/516; 549/59; 549/462
(58) Field of Search ............... 548/512, 516; 514/413

(56) References Cited

U.S. PATENT DOCUMENTS

| | | | |
|---|---|---|---|
| 3,705,905 A | 12/1972 | Culvenor et al. | |
| 4,546,100 A | 10/1985 | Fabre et al. | |
| 4,684,658 A | 8/1987 | Fabre et al. | |
| 5,260,451 A | * 11/1993 | Dannhardt et al. ......... | 548/453 |

FOREIGN PATENT DOCUMENTS

| | | |
|---|---|---|
| DE | 198 45 446 | 4/2000 |
| WO | 95/32970 | 12/1995 |
| WO | 95/32971 | 12/1995 |
| WO | 95 32972 | 12/1995 |

OTHER PUBLICATIONS

Gerd Dannhardt et al.: "Oxidative ringoeffnung von 6.7–Diphenyl–2.3–dihydro–1H–pyrrolizin (DADHP) durch m–chlorperbenzoesaeure" Arch. Pharm., vol. 319, pp. 231–234, 1986.

Gerd Dannhardt et al.: "Natriummetaperiodat–oxidation von 6.7–Diphenyl–2.3–dihydro–1H–pyrrolzin" Arch. Pharm., vol. 318, pp. 661–663, 1985.

Gerd Dannhardt et al.: "6.8–Diaryl–2.3–dihydro–1H–pyrrolizine (DADHP) als singulett–sauerstoff–faenger" Arch. Pharm., vol. 318, pp. 663–664, 1985.

Gerd Dannhardt et al.: Synthese und oxidation von 6.7–diphenyl–2.3–dihydro–1H–pyrrolizin–5–yl–acetaldehyd (DADHP–5–acetaldehyd) Arch. Pharm., vol. 319, pp. 500–505, 1986.

Gerd Dannhardt et al.: "6.7–diarylsubstituierte 1– und 3–pyrrolizinone (1–DAPON und 3–DAPON)" Arch. Pharm., vol. 319, pp. 749–755, 1986.

G. Dannhardt et al.: "C–5 functionalized 6,7–diphenyl–2,3–dihydro–1H–pyrrolizines as inhibitors of bovine cyclooxygenase and 5–lipoxygenase" Arch. Pharm., vol. 327, pp. 509–514, 1994.

Stefan Laufer et al.: "Synthesis and evaluation of a novel series of pyrrolizine derivatives as dual cyclooxygense–1 and 5–lipoxygenase inhibitors" Arch. Pharm. Pharm. Med. Chem., vol. 330, pp. 307–312, 1997.

Joseph M. Muchowski et al.: "Synthesis and anti–inflammatory and analgesic activity of 5–aroyl–1, 2–dihydro–3H–pyrrol[1,2–a]pyrrole–1–carboxyoic acids. The 6–substituted compounds" J. Med. Chem., vol. 30, pp. 820–823, 1987.

Stefan A. Laufer et al.: "(6, 7–diaryldihydropyrrolizin–5–yl)acetic acids, a novel class of potent dual inhibitors of both cyclooxygenase and 5–lipoxygenase" J. Med. Chem., vol. 37, pp. 1894–1897, 1994.

"Antiinflammatory cyclooxygenase and 5–lipoxygenase inhibitor" Drugs of the Future, vol. 20, No. 10, pp. 1007–1007, 1995.

Gerd Dannhardt et al.: "Synthese und eigenschaften von 2,3–dihydro–1H–pyrrolizinen" Arch. Pharm., vol. 312, pp. 896–905, 1979.

Gerd Dannhardt et al.: "Stellungsisomere diaryldihydropyrrolizinyl–essigsaeuren und –hydroxethyl–derivate" Arch. Pharm. vol. 321, pp. 159–162, 1988.

* cited by examiner

*Primary Examiner*—Joseph K. McKane
*Assistant Examiner*—Golam M M Shameem
(74) *Attorney, Agent, or Firm*—Oblon, Spivak, McClelland, Maier & Neustadt, P.C.

(57) ABSTRACT

The present invention relates to compounds of the formula I

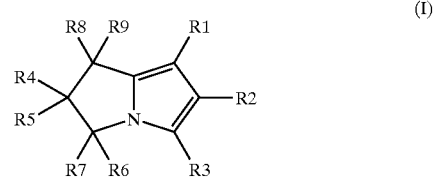

in which one of the radicals R8 and R9 is a hydrogen atom or an alkyl group and the other is hydroxyl, alkoxy or acyloxy or where R8 and R9, together with the carbon atom to which they are bonded, are a carbonyl group and the radicals R1 to R7 have the meanings indicated in the description.

The compounds inhibit the release of various mediators of the arachidonic acid cascade and can thus be used for the prevention of allergically induced disorders or for the treatment of disorders of the rheumatic type.

11 Claims, No Drawings

ANTI-INFLAMMATORY OXO DERIVATIVES AND HYDROXY DERIVATIVES OF PYRROLIZINES, AND THEIR PHARMACEUTICAL USE

The present invention relates to antiinflammatory oxo and hydroxy derivatives of pyrrolizines, pharmaceutical compositions which contain these compounds and their use in pharmacy.

Pharmacologically active pyrroliuine compounds which inhibit 5-lipoxygenase (5-LO) and cyclooxygenase 1 and 2 (Cox-1 and Cox-2) are already known. For example, pyrrolizine compounds having anti-inflammatory activity are described in Arch. Pharm. 319, 231–234 (1986); 318, 661–663 (1985); 318, 663–664 (1985); 319, 500–505 (1986); 319, 749–755 (1986); 327, 509–514 (1994); 330, 307–312 (1997) and in J. Med. Chem. 1987, 30, 820–823 and 1994, 37, 1894–1897. The most promising compound of this type is the 6-(4-chlorophenyl)-7-phenyl-2,3-dihydropyrrolo-[1,2-a]pyrrole compound ML 3000, see Drugs of the Future, 1995, 20 (10): 1007–1009. It suppresses the release of leukotrienes, thromboxanes and prostaglandins. The inhibitory action on the formation of the leukotrienes and the prostaglandins is balanced in this structure, and harmful effects of a pure inhibitory action on cyclooxygenase 1 and 2 (Cox-1 and Cox-2) with increased formation of leukotrienes are not observed here. In all these compounds, the 1-position of the pyrrolizine structure is unsubstituted.

Further pyrrolizine compounds are described in U.S. Pat. No. 5,260,451 and in WO 95/32970; WO 95/32971; and WO 95/32972. These compounds have the structural formula

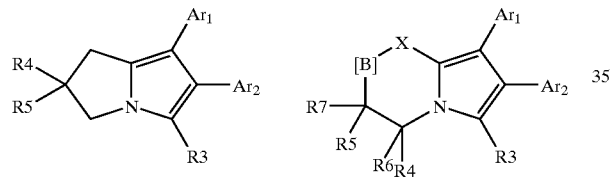

A fused diarylpyrrole structural element and a third acidic radical R3 is common to all compounds. The compounds are distinguished by high lipophilicity, good bioavailability and medium half-lives.

According to the general disclosure in WO 95/32970 and WO 95/32971, X can be a carbonyl group. Compounds of this type, however, cannot be prepared according to the processes described in the abovementioned WO publications and in US 5,260,451.

U.S. Pat. No. 3,705,905 discloses compounds of the formula

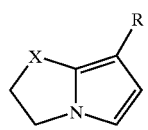

in which X is methylene, α- or β-hydroxyethylene or carbonyl and R is a hydroxymethyl group or a formyl group. These compounds have antiviral, antitumor or immunosuppressive activity.

Further pyrrolizine compounds which can be used for the treatment of thrombotic disorders are disclosed in U.S. Pat. No. 4,546,100 and U.S. Pat. No. 4,684,658.

It was an object of the present invention to make available compounds which, in comparison with the prior art, likewise exert a balanced action at a high level on the two key enzyme systems of the arachidonic acid cascade, namely 5-lipoxygenase and the cyclooxygenases.

Surprisingly, it has now been found that this object is achieved by pyrrolizine compounds which in various positions of the ring skeleton have oxygen functions as polarity-increasing groups, such as a carbonyl group, a hydroxy group or an alkoxy group.

The present invention therefore relates to pyrrolizine compounds of the formula I

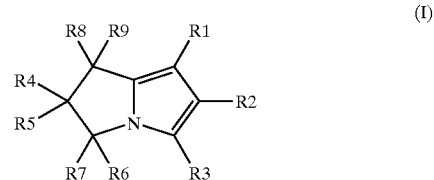

in which
R1 and R2, which can be identical or different, are aryl or an aromatic mono- or bicyclic, heterocyclic radical which has 1, 2 or 3 heteroatoms which independently of one another are selected from N, O and S, where the radicals $R^1$ and R2 can optionally be substituted by 1, 2 or 3 groups, which independently of one another are selected from alkyl, halogen, $CF_3$, hydroxy, alkoxy, aryloxy and CN, and can optionally be fused to phenyl or naphthyl;
R3 is H, alkyl, COOH, COOalkyl, COOAlkPh, COCOOalkyl, CHO or A—Y, where
A is $C_1$–C-alkylene or $C_2$–$C_8$-alkenylene, which can optionally be substituted by hydroxyl or alkoxy,
Y is COOH, $SO_3H$, $OPO(OH)_2$, $OP(OH)_2$, tetrazolyl, COOalkyl, $SO_3$alkyl, CHO or OH;
Alk is $C_1$–$C_4$-alkylene;
R4, R5, R6 and R7, which can be identical or different, are H, alkyl, hydroxyalkyl or alkoxyalkyl;
one of the radicals R8 and R9 is H, alkyl, hydroxyalkyl or alkoxyalkyl and the other is hydroxyl, alkoxy, carboxyl or acyloxy or R8 and R9, together with the carbon atom to which they are bonded, are a carbonyl group,
and the optical isomers, physiologically tolerable salts and physiologically readily hydrolyzable esters thereof.

The physiologically tolerable salts can in the present case be acid addition salts or base addition salts. For acid addition salts, inorganic acids, such as hydrochloric acid, sulfuric acid or phosphoric acid, or organic acids, such as tartaric acid, lactic acid, citric acid, malic acid, mandelic acid, ascorbic acid, maleic acid, fumaric acid, gluconic acid and the like, are used.

The base addition salts include salts of the compounds of the formula I with inorganic bases, such as sodium hydroxide or potassium hydroxide or with organic bases, such as mono-, di- or triethanolamine.

Physiologically readily hydrolyzable esters of the compounds of the formula I are, for example, alkyl, pivaloyloxymethyl, acetoxymethyl, phthalidyl, indanyl and methoxymethyl esters.

If the compounds according to the invention have asymmetric centers, racemates and optical isomers (enantiomers, diastereomers) are included.

The expression "alkyl, alkoxy etc." includes straight-chain or branched alkyl groups, such as methyl, ethyl, n- and i-propyl, n-, i- or t-butyl, n-pentyl, neopentyl, n-hexyl etc. Unless stated otherwise, "alkyl" is preferably $C_1$–$C_8$-alkyl, in particular $C_1$–$C_5$-alkyl and particularly preferably $C_1$–$C_4$-alkyl.

"Aryl" is preferably naphthyl and in particular phenyl.

The expression "halogen" includes a fluorine, chlorine, bromine or iodine atom and in particular a fluorine or chlorine atom.

"Alkylene" or "alkenylene" represents straight-chain or branched alkylene or alkenylene groups preferably having 1 to 6 or 2 to 6 and in particular 1 to 4 or 2 to 4 carbon atoms. The alkylene group and in particular the methylene group is preferred.

"Acyl" represents RCO, where R preferably has the meanings stated above for "alkyl" and "aryl". Acetyl is particularly preferred.

The "aromatic heterocyclic radical" is in particular a 5- and 6-membered heterocyclic radical, which can be substituted and fused as indicated above. Examples are a thiophene, pyrrole, imidazole, thiazole, thiadiazole, furan, oxazole, isoxazole, pyridine, pyrimidine, benzofuran or quinoline radical. If the heterocycle is substituted, 1, 2 or 3 substituents are present which are selected from halogen, $CF_3$, $C_1$–$C_8$-alkyl and $C_1$–$C_8$-alkoxy. A thiophene radical or halogen radical, in particular chlorine-substituted, thiophene radical, a furan radical, pyridine radical, benzofuran radical or quinoline radical is preferred.

The substituents of the aryl group are preferably selected from halogen, in particular fluorine or chlorine, and $CF_3$. If the aryl group is a phenyl ring, the substituents are preferably situated in the m- and/or p-position.

Particularly preferably, R1 and R2 are phenyl, halogen-substituted phenyl (substituted by 1 or 2 halogen atoms, in particular chlorine atoms), hydroxy- or alkoxy-substituted phenyl (substituted by 1 or 2 hydroxy or alkoxy groups), thienyl or benzofuranyl. Especially preferably, R1 is phenyl and R2 is phenyl which is substituted by 1 or 2 halogen atoms, in particular chlorine atoms, or 1 or 2 hydroxy groups.

Compounds of the formula I in which R3 is COOalkyl, COOAlkphenyl, COCOOalkyl or A—Y, where A and Alk have the meanings indicated above and Y is COOalkyl, $SO_3$alkyl or OH, are intermediates which can be used for the preparation of the pharmacologically active compounds of the formula I. Pharmacologically active compounds of the formula I are thus those in which R3 is H, alkyl, COOH, CHO or A—Y, where A has the meanings indicated above and Y is COOH, $SO_3$H, $OPO(OH)_2$, $PO(OH)_2$, CHO or tetrazolyl.

Preferably, R3 is H, alkyl, COOH, CHO or A—Y, where A is $C_1$–$C_8$-alkylene which is optionally substituted by OH, and Y is COOH.

The radicals R6 and R7 are preferably H and the radicals R4 and R5 are preferably alkyl, in particular methyl.

A preferred embodiment is compounds of the formula I in which R1 is phenyl, R2 is phenyl, which is substituted by 1 or 2 halogen atoms, in particular chlorine atoms, and/or 1 or 2 hydroxy and/or alkoxy groups; R3 is H, COOH, CHO, $CH_2COOH$ or CH(OH)COOH; and R4 to R9 have the meanings indicated above.

A further embodiment is compounds of the formula I in which at least one of the radicals R4, R5, R6 and R7 is hydroxyalkyl, in particular hydroxymethyl, and the remainder of the radicals R4, R5, R6 and R7 independently of one another are H or alkyl. Preferably, R4 is hydroxyalkyl, in particular hydroxymethyl, R5 is H or alkyl and R6 and R7 independently of one another are H or alkyl. R1, R2 and R3 preferably have the meanings indicated in the preceding paragraph.

Scheme A shows various strategies for the introduction of such polarity-increasing functional groups into the skeleton of the pyrrolizine parent structure and its derivatives (A–F).

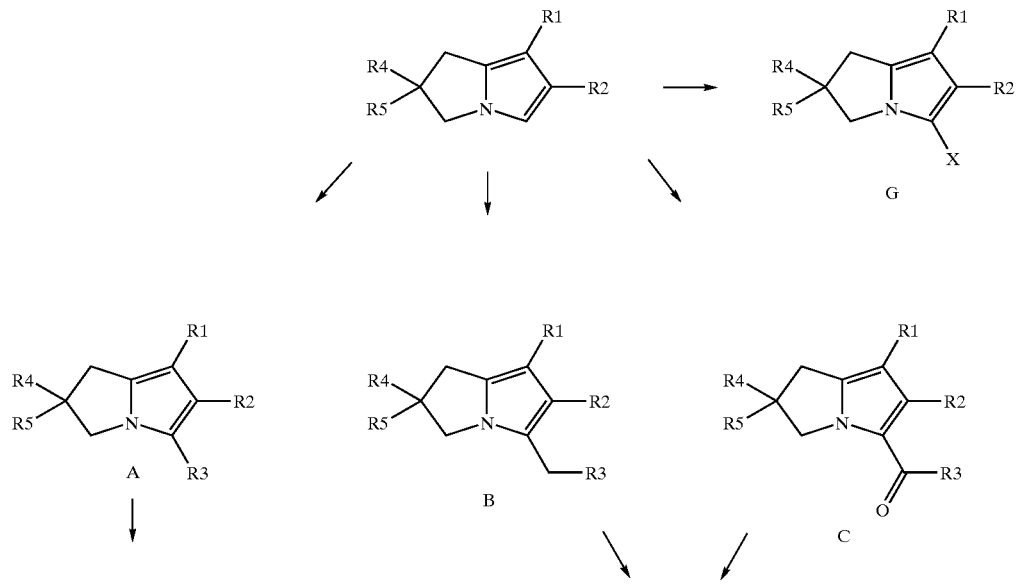

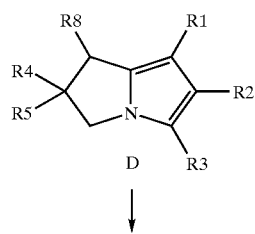

D

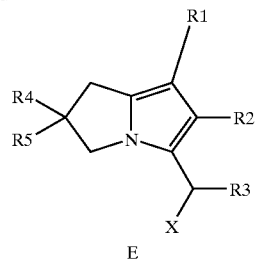

E

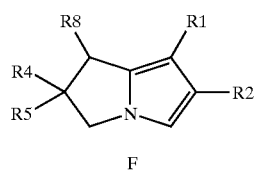

F

The compounds according to the invention can be prepared by oxidation in the 1-position. Starting compounds which can be used here are compounds of the formula II, see the following synthesis scheme 1. The compounds of the formula II are prepared according to the S processes described in the abovementioned prior art and in particular according to the processes described in U.S. Pat. No. 5,260,451 and WO 95/32970, WO 95/32971 and WO 95/32972.

For the preparation of compounds of the formula I in which R3 is COOH, COOalkyl, COOAlkphenyl, COCOOalkyl or CHO, the compounds of the formula II are reacted in a known manner with N-bromosuccinimide (NBS) in the presence of a free-radical initiator, such as azobisisobutyronitrile, in a chlorinated solvent, such as carbon tetrachloride. The reaction temperature is chosen such that the free-radical reaction proceeds, for example, at 70 to 90° C. When using 1 mole equivalent of N-bromosuccinimide, the compound of the formula III brominated in the 1-position is obtained. This, in turn, can then be reacted with acylates, for example sodium acetate, or alkoxides, such as sodium methoxide or sodium ethoxide, to give the corresponding compounds of the formula Ic and Id. The reactions are carried out in a known manner; the reaction with the acylates is carried out in an inert solvent, for example dimethylformamide (DMF), at 70 to 90° C. The reaction of the compounds of the formula III with alkoxides is expediently carried out in the corresponding alcohol. Alternatively, the compounds of the formula III can be reacted, without being isolated from the reaction mixture, directly with an alcohol to give the compounds of the formula Ib.

Alternatively, a compound of the formula II can be reacted with one mole equivalent of NBS in a chlorinated solvent in the presence of water to give a compound of the formula Ia. Using a further mole equivalent of NBS, a compound of the formula Ib is then obtained.

In the synthesis schemes, acyl has the meanings indicated above. R is an alkyl radical.

Synthesis scheme 1:

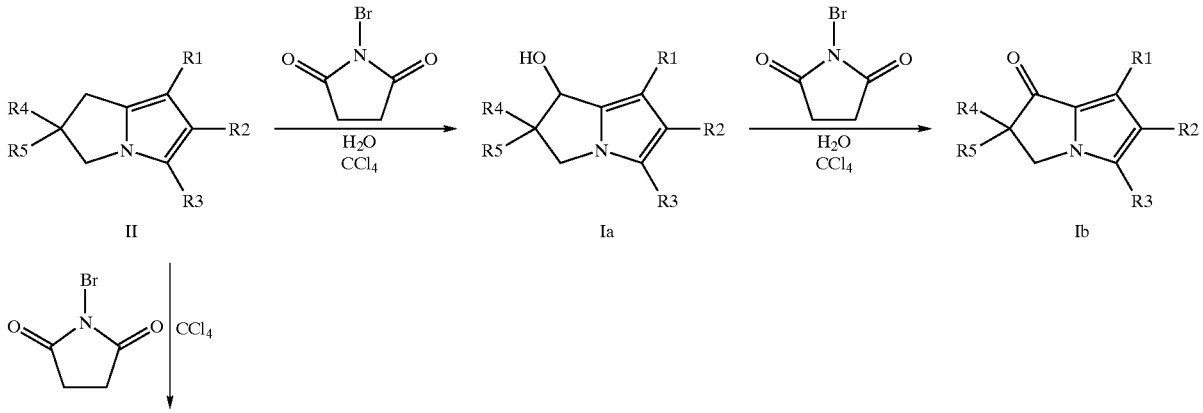

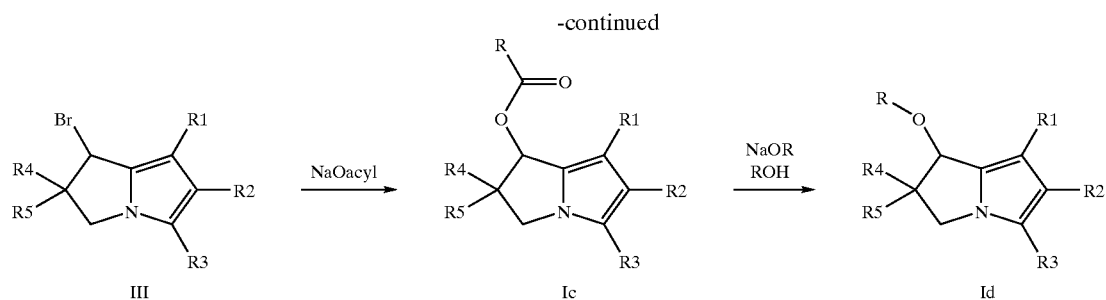

Compounds of the formula I according to the invention in which R3 is a hydrogen atom are preferably attacked by oxidizing agents on the pyrrole nucleus, see Arch. Pharm. 318, 661–663 (1985); 663–664 (1985); 319, 231–234 (1986) and 312, 896–907 (1985). Compounds of the formula I in which R3 is an aliphatic radical (for example $CH_2COOH$, $CH_3$) are preferably attacked at this aliphatic substituent. For the preparation of compounds of the formula I in which R3 is a hydrogen atom, the reactive 5-position is therefore firstly blokked. As shown in synthesis scheme 2, this is carried out starting from compounds of the formula V, whose preparation is likewise described in the abovementioned prior art and in particular in U.S. Pat. No. 5,269,451 and WO 95/32970, WO 95/32971 and WO 95/32972, by introduction of an acyl function. For this purpose, a compound of the formula V is reacted with trichloromethyl chloroformate in an inert solvent, for example tetrahydrofuran or dioxane, and the intermediately contained ester is reacted with methanol, a compound of the formula VI being obtained. This is then reacted analogously to synthesis scheme 1 with 2 mole equivalents of N-bromosuccinimide in carbon tetrachloride and in the presence of water to give a compound of the formula Ie. By means of basic ester cleavage in a customary manner, for example using potassium hydroxide in methanol or water, the carboxylic acid of the formula Is is obtained. This, in turn, can be decarboxylated at 250 to 350° C. to give a compound of the formula Ig (R3=H). The compounds of the formula Ig can then be functionalized using customary methods at position 5, for example by Vilsmeyer formylation with phosphorus oxychloride in dimethylformamide (DMF) to give a compound of the formula Is. Alternatively, the keto group in the 1-position of the compound Ig can be reduced to the alcohol function, for example using complex hydrides, such as lithium aluminum hydride. The alcohol function in the is 5-position can then be etherified or esterified in a customary manner, compounds of the formula Ic and Id (R3=H) being obtained.

Alternatively, the compound of the formula VI can be reacted with one mole equivalent of N-bromosuccinimide and then with an alkoxide to give a compound of the formula Ii. By means of ester cleavage and decarboxylation in the manner indicated above, the compounds of the formula Ij and Ik are obtained.

Synthesis scheme 2:

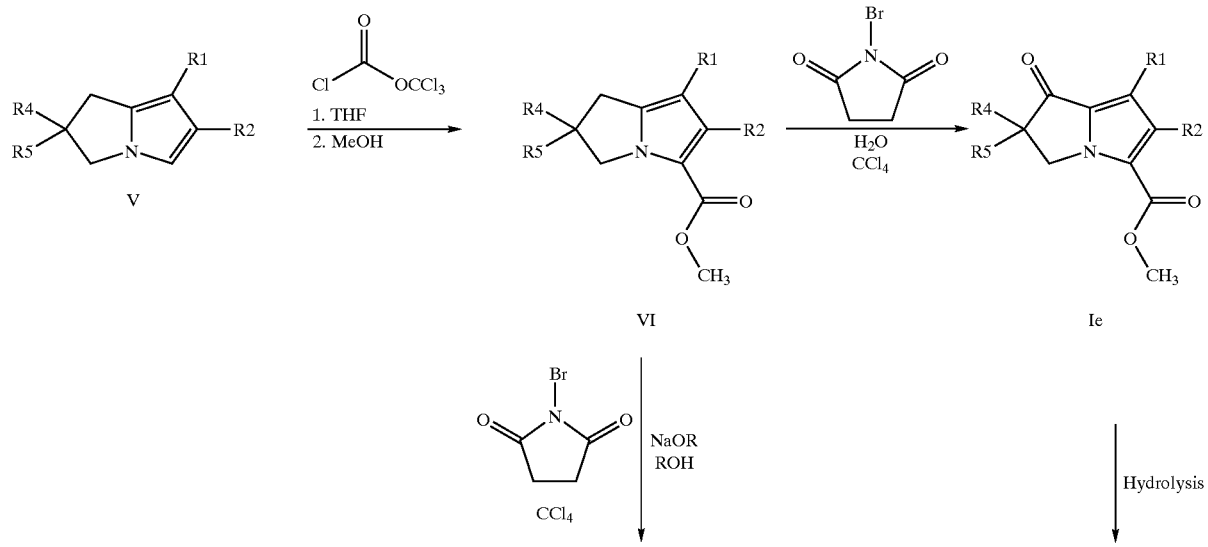

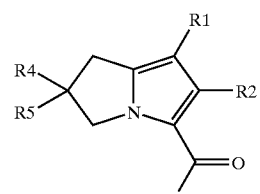
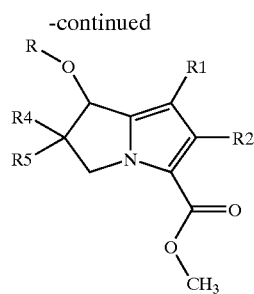
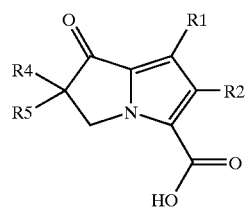

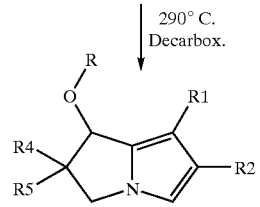
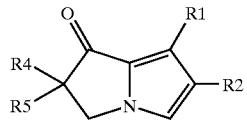

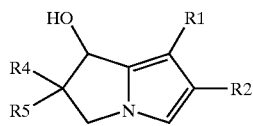
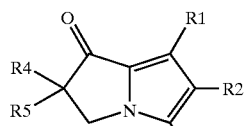

An alternative for the introduction of an acyl function into a compound of the formula V consists in the route shown in synthesis scheme 3. In this, a compound of the formula V is reacted with ethyl oxalyl chloride in an inert solvent, such as THF or dioxane, to give a compound of the formula XV. This, in turn, is oxidized, as already described in connection with synthesis scheme 2, with 2 mole equivalents of N-bromosuccinimide to give a compound of the formula Il which, after hydrolysis (basic ester cleavage as described above), affords a compound of the formula Im. Alternatively, a compound of the formula XV can be reacted with one mole equivalent of N-bromosuccinimide and then with an alkoxide to give a compound of the formula In, which can be hydrolyzed to the free acid Io in the customary manner. The compound of the formula Io can further be derivatized by reduction of the α-keto group of the substituent in the 5-position by Huang Minion reduction with hydrazine and base. A compound of the formula Ip is obtained here. Reduction of a compound of the formula Io using a complex hydride, for example sodium borohydride in water or an aqueous alcohol, affords the compound Iq.

Synthesis scheme 3:

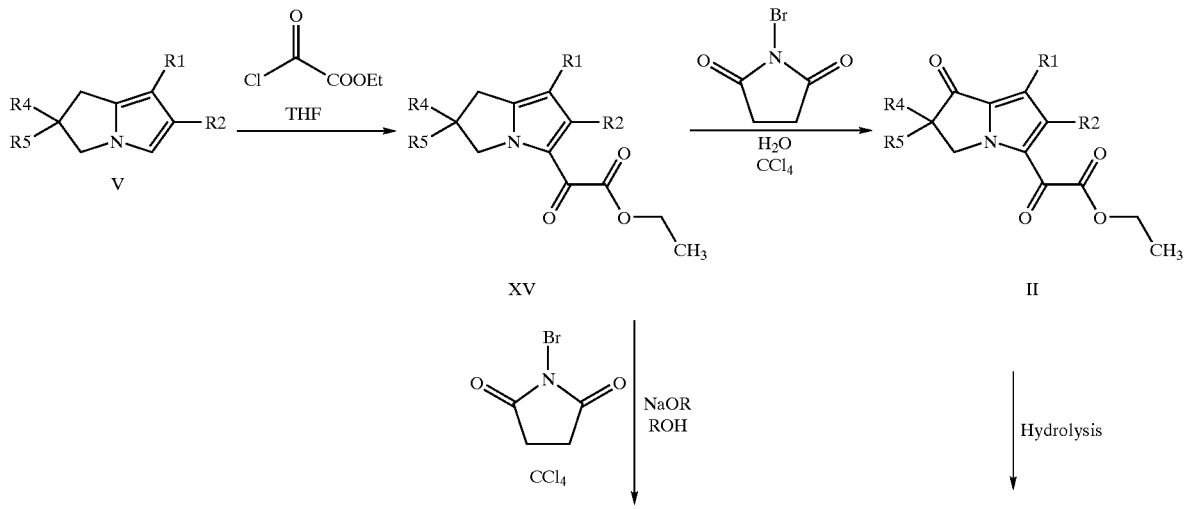

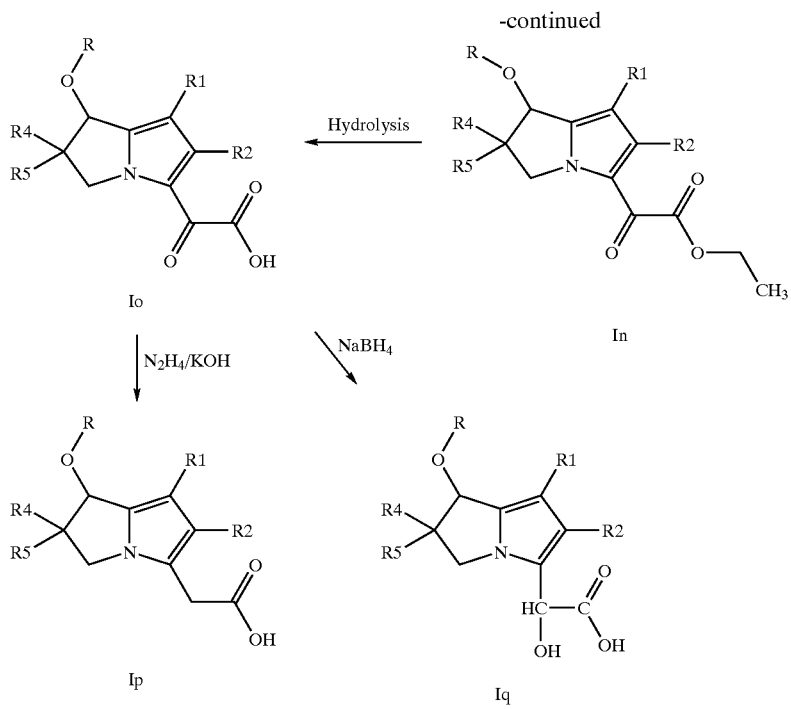

The oxidative attack of N-bromosuccinimide already mentioned above on aliphatic substituents in the 5-position of the compounds according to the invention can be prevented by introduction of highly space-filling protective groups in the area of this position. The synthesis is carried out here starting from compounds of the formula IV, whose preparation is likewise described in the abovementioned prior art and in particular in U.S. Pat. No. 5,260,451 and WO 95/32970, WO 95/32971 and WO 95/32972, according to the processes described in synthesis scheme 4. In these processes, a compound of the formula IV is esterified with a highly branched alcohol, such as t-butanol or neopentyl alcohol, in the presence of an activating agent, for example carbonyldiimidazole, in an inert solvent, such as tetrahydrofuran or dioxane, to give a compound of the formula XXI. The ester XXI is converted, as described in connection with synthesis scheme 2, with 2 mole equivalents of N-bromosuccinimide into a compound of the formula Ir which, after ester cleavage and decarboxylation, affords a compound of the formula Is or It. Alternatively, the ester XXI can be reacted with one mole equivalent of N-bromosuccinimide and then with alkoxide to give a compound of the formula Iu. Ester hydrolysis and decarboxylation then affords a compound of the formula Iv and Iw.

Synthesis scheme 4:

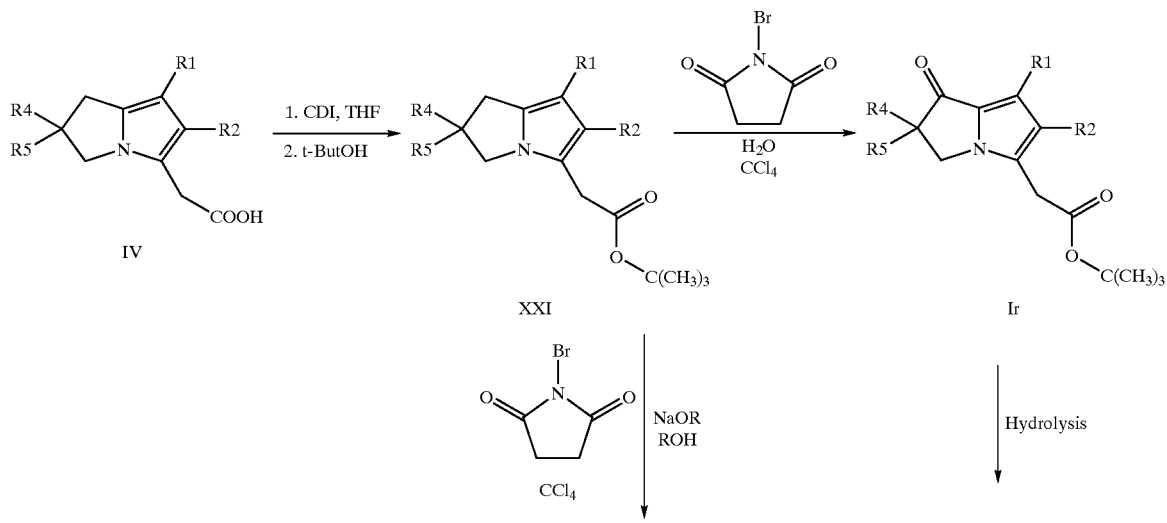

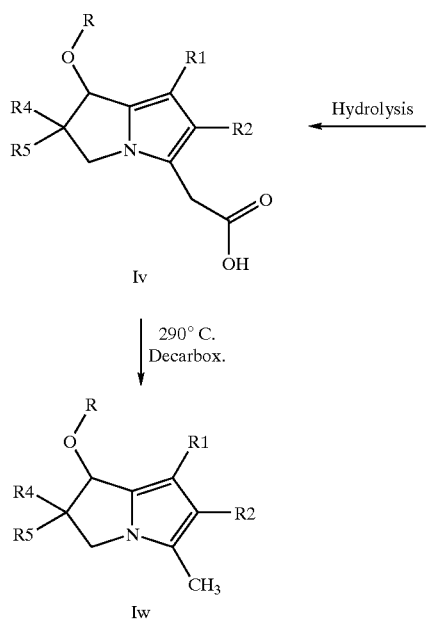
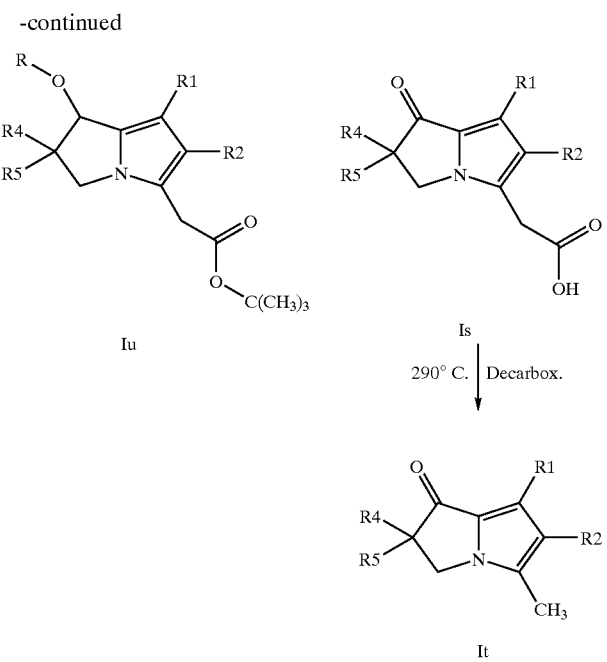

The introduction of polar groups, such as X or R8=hydroxyl, R8 and R9=carbonyl and R8=carboxyl, requires a modified synthesis strategy. Such functional groups cannot be subsequently introduced onto the hydrocarbon structure of the ring to be fused. Preparation is carried out by means of suitable precursors which already contain these functional groups, protected by 'protective groups' (Pg)

Scheme B

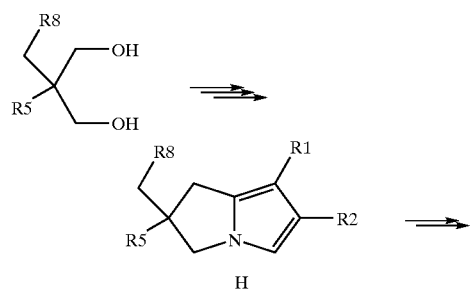

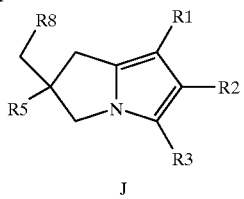

Synthesis scheme 5 shows an example of how, applying the methodology described in EP 0397175 (XXXVI–XXXVIII, starting from trishydroxymethylene derivatives (XXXIII, X=OH) by selective introduction of a protective group for one of the 3 hydroxymethylene groups, compounds of the structure H and J can be obtained which exhibit the corresponding substitution pattern. Compounds of the structure H and J likewise occur in the form of two optical antipodes which, if required, [lacuna] by application of chromatographic techniques or by preparation of diastereomeric synthesis intermediates (acetals or ketals with R=H, R'=alkyl, aryl etc., or R=R'=alkyl, aryl etc.), which, after cleavage, yield the pure enantiomers of the precursors.

Synthesis scheme 5

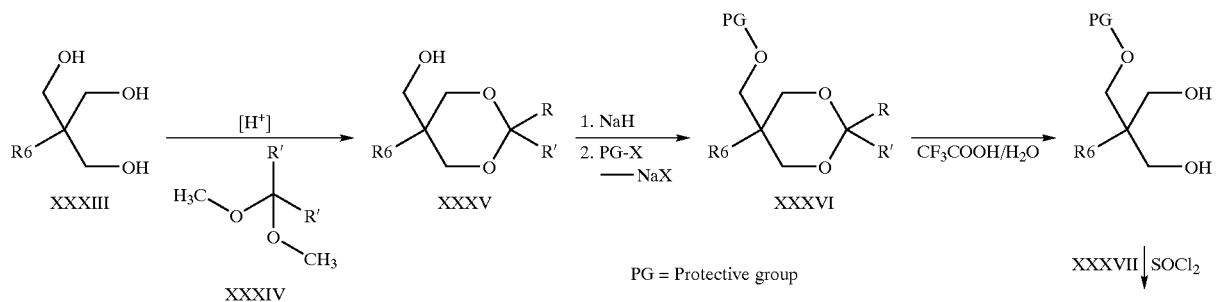

PG = Protective group

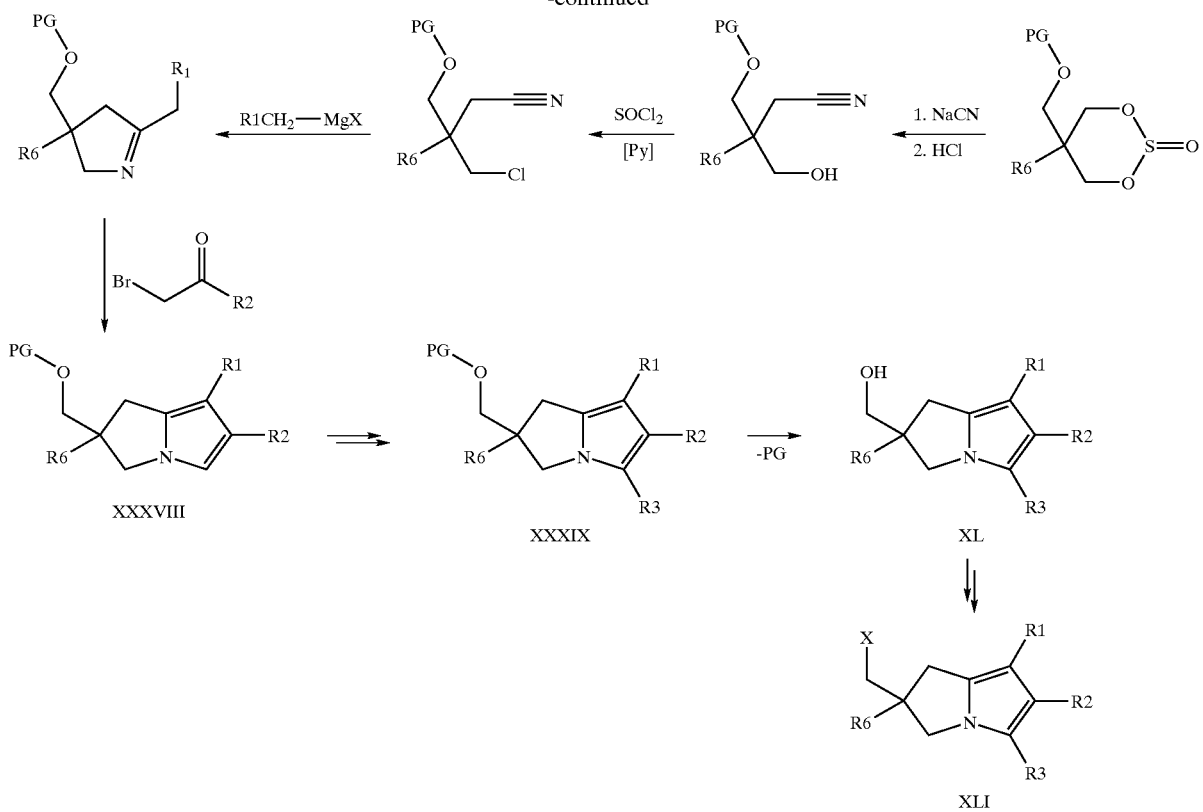

The introduction of a hydroxy group (scheme A: structure G (X=OH) into the pyrrole moiety of the pyrrolizine parent structure yields compounds (XXIX in synthesis scheme 6) which are in equilibrium with tautomeric oxo compounds. In the case of the pyrrolizines, these compounds can only be isolated in the form of stable derivatives. They undergo rapid conversion by oxidation with atmospheric oxygen. Synthesis scheme 6 describes how, on pyrrolizines having structure V, which have been metalated, stable esters of the corresponding hydroxy derivatives can be obtained directly by the action of organic peroxides.

Synthesis scheme 6

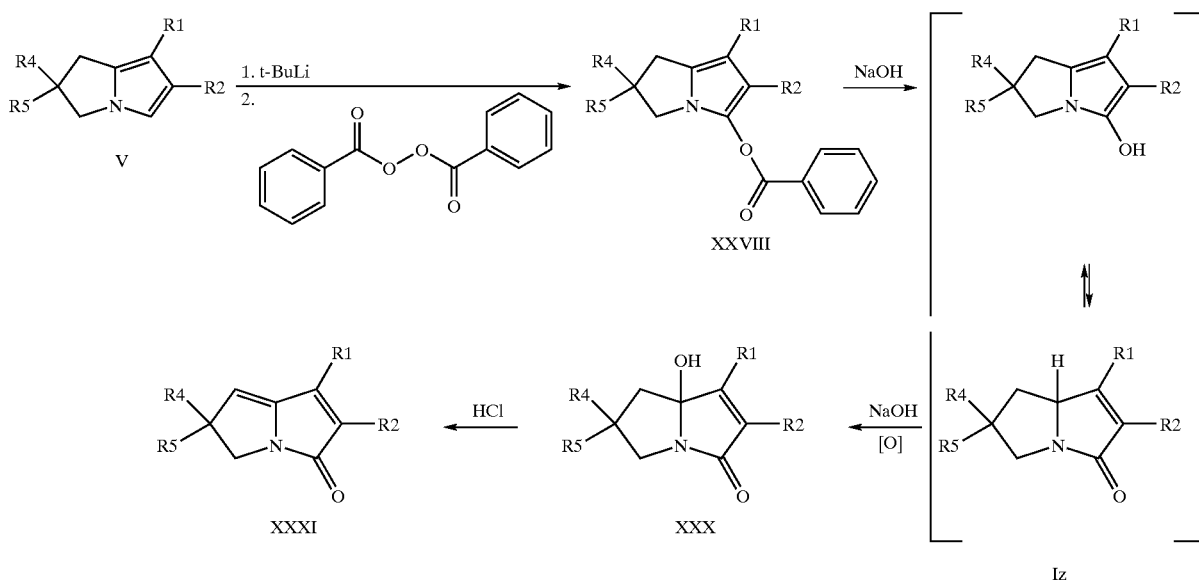

Synthesis scheme 7 demonstrates that substituents in position 5 (such as the acetic acid side chain $R^3$=$CH_2COOH$, IIa) also form the acyloxy derivatives of the underlying pyrrolizines (structure XXXII) by treatment with carboxylic acids in the presence of $BF_3$ etherate.

Synthesis scheme 7

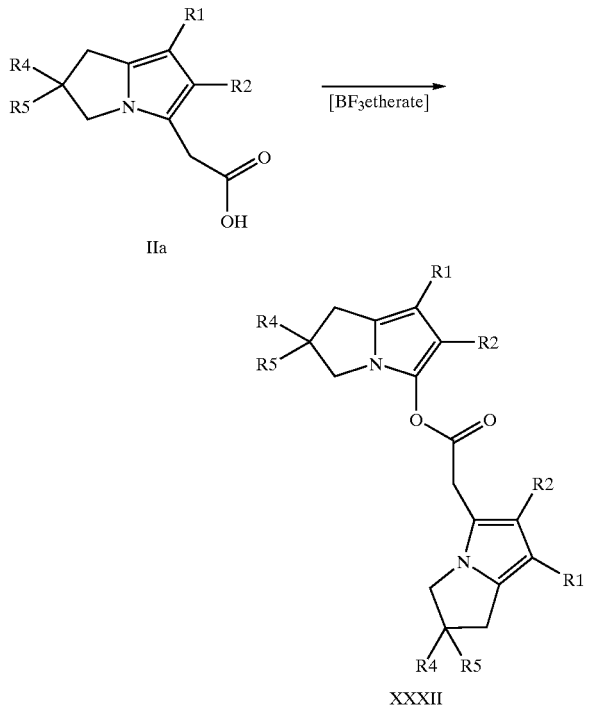

The compounds according to the invention show in vitro and in vivo inhibition of the release of various mediators of the arachidonic acid cascade, in particular of 5-lipoxygenase and of cyclooxygenases 1 and 2 and therefore a marked antiinflammatory activity. They are thus suitable for the treatment of disorders in which increased release rates of the eicosanoid mediators are responsible for the development or the progressive course of these disorders. In particular, the compounds according to the invention can be used for the treatment of disorders of the rheumatic type and for the prevention of allergically induced disorders. The compounds according to the invention are thus efficacious antiinflammatories, analgesics, antipyretics, antiallergics and broncholytics and can therefore be used for the prophylaxis of anaphylactic and septic shock, and for the treatment of dermatological disorders, such as psoriasis, urticaria, acute and chronic exanthema of allergic and nonallergic genesis.

The compounds according to the invention have increased chemical stability, parenteral administrability, improved enteral bioavailability and shorter half-lives.

The compounds according to the invention can be administered either as individual therapeutic active compounds or as mixtures with other therapeutic active compounds. They can be administered as such, but in general they are administered in the form of pharmaceutical compositions, i.e. as mixtures of the active compounds with suitable pharmaceutical carriers or diluents. The compounds or compositions can be administered orally or parenterally, but preferably they are given in oral dosage forms.

The nature of the pharmaceutical composition and of the pharmaceutical carrier or diluent depends on the desired manner of administration. Oral compositions can be present, for example, as tablets or capsules and can contain customary excipients, such as binders (e.g. syrup, acacia, gelatine, sorbitol, tragacanth or polyvinylpyrrolidone), fillers (e.g. lactose, sugar, cornstarch, calcium phosphate, sorbitol or glycine), lubricants (e.g. magnesium stearate, talc, polyethylene glycol or silica), disintegrants (e.g. starch) or wetting agents (e.g. sodium lauryl sulfate). Oral liquid preparations can be present in the form of aqueous or oily suspensions, solutions, emulsions, syrups, elixirs or sprays etc. or can be present as dry powders for reconstitution with water or another suitable carrier. Liquid preparations of this type can contain customary additives, for example suspending agents, flavorings, diluents or emulsifiers. For parenteral administration, solutions or suspensions with customary pharmaceutical carriers can be employed.

The compounds or compositions according to the invention can be administered to a mammal (human and animal) in doses of approximately 0.5 mg to approximately 100 mg per kg of body weight per day. They can be administered in an individual dose or in a number of doses.

The spectrum of action of the compounds was investigated with the aid of the following test systems:

Test System for Determination of the Inhibition of 5-Lipoxygenase

Human granulocytes are used as a source of 5-lipoxygenase. By means of stimulation with calcium ionophore A 23187, $LTB_4$ (leukotriene $B_4$) is formed from endogenous arachidonic acid. The granulocytes are isolated and the enzyme reaction is carried out according to known processes (see Arch. Pharm. Med. Chem. 330, 307–312 (1997)).

The blood, protected from clotting with heparin, is centrifuged over a discontinuous Percoll® gradient and the granulocyte layer is removed by pipette. After lysis of the erythrocytes, the granulocytes are washed a number of times and then adjusted to a specific cell count. The enzyme reaction is then started in the presence or absence of the test substance after addition of $Ca^{2+}$ using calcium ionophore A 23181. The synthesis of the leukotrienes is stopped after 1.5 minutes. The samples are centrifuged off and the supernatant is diluted. $LTB_4$ is determined quantitatively by means of ELISA.

Test System for Determination of the Inhibition of Cyclooxygenase-1

In this test system, the amount of prostaglandin $E_2$ formed from human platelets after addition of calcium ionophore is determined by means of ELISA. In this process, the platelets are obtained after centrifugation over a discontinuous Percoll® gradient. The enzyme reaction and the determination of the metabolites formed is carried out in principle as in the determination of 5-lipoxygenase inhibition. Differences exist with respect to the incubation time. Furthermore, the addition of a thromboxane synthase inhibitor is necessary (see Arch. Pharm. Med. Chem. 330, 307–312 (1997)).

Test System for Determination of the Inhibition of Cyclooxygenase-2

$COX_2$ (from sheep placenta) is preincubated with test substance at 4° C. for 10 min, then stimulated with arachidonic acid (5 μM) at 25° C. for 10 min. The reference used is diclofenac ($IC_{50}$ ($COX_2$)=3.0 $10^{-6}$ M). The determination is carried out at 3 dilutions ($10^{-7}$, $10^{-6}$, $10^{-5}$ M), and the $PGE_2$ concentrations are quantified by means of ELISA (see Mitchell, J. A. et al. Proc. Nat. Acad. Sci 90: 11693–11697 (1993)).

Determination of the Partition Coefficient

The partition coefficient P of the compounds was determined in the system n-octanol/water according to the OECD Guidline for Testing Chemicals, No. 117.

The results are compiled in table 1 below.

TABLE 1

IC$_{50}$ (in μmol) and log P values

| Example | Structure | COX-1 | COX-2 | 5-LO | Log P pH 2.5 | Log P pH 7.5 |
|---------|-----------|-------|-------|------|--------------|--------------|
| 16 | (structure) | 0.5 | 7.5 | 0.06 | 5.1 | 6.7 |
| 14 | (structure) | 0.06 | — | 0.04 | 4.5 | 1.7 |
| 6 | (structure) | 0.95 | — | 0.23 | 5.0 | 5.1 |
| 18 | (structure) | 0.046 | 2.1 | 2.3 | 3.3 | 1.1 |
| | ML 3000 | 0.21 | 4.7 | 0.18 | 4.8 | 1.9 |

The following examples illustrate the invention without restricting it.

In the examples, the following abbreviations are used:

| | |
|---|---|
| THF | tetrahydrofuran |
| MeOH | methanol |
| NBS | N-bromosuccinimide |
| DMSO | dimethyl sulfoxide |
| DMF | dimethylformamide |
| AIBN | azobisisobutyronitrile |
| M.p. | melting point |

EXAMPLE 1

Methyl 6-(4-Chlorophenyl)-2,3-dihydro-1-methoxy-
2,2-dimethyl-7-phenyl-1H-pyrrolizin-5-yl]
carboxylate a) Methyl 6-(4-Chlorophenyl)-2,3-dihydro-2,2-dimethyl-7-phenyl-1H-pyrrolizin-5-yl]carboxylate (6-(4-Chlorophenyl)-2,3-dihydro-2,2-dimethyl-7-phenyl-1H-pyrrolizine (10.0 g, 31.1 mmol, prepared according to Laufer et al. (J. Med. Chem. 1994, 37, 1894–1897) and 3.3 g of dry triethylamine are dissolved in 30 ml of absolute THF. A solution of 3.1 g (15.7 mmol) of trichloromethyl chloroformate (diphosgene) in 20 ml of THF is then slowly added dropwise at room temperature and the mixture is stirred for 7 h. 30 ml of MeOH are then added. The mixture is stirred again at room temperature for 12 h. The product precipitates as a pale green solid. It is filtered off from the solvent with suction and washed with a little MeOH. The mother liquor, mixed with 200 ml of water, yields, after ultrasonic treatment (10 min.), a second crystal fraction. The fractions thus obtained are purified by stirring with MeOH.

Total yield: 9.94 g (84%), $C_{23}H_{22}ClNO_2$, 379.9 g/mol,
M.p.: 170° C.
IR (KBr): 1/l (cm−1), 2945, 1708 (CO ester), 1466, 1406, 1216, 1119, 1098, 831, 777, 702, 696.
$^1$H-NMR (CDCl$_3$): d (ppm)=7.26–7.11 (m, 7H, ph +AA'), 6.99–6.94 (BB', 2H), 4.14 (s, 2H, CH$_2$), 3.65 (s, 3H, OCH$_3$), 2.84 (s, 2H, CH$_2$), 1.31 (s, 6H, C(CH$_3$)$_2$).
$^{13}$C-NMR (CDCl$_3$): d (ppm)=161.6 (C̲O), 140.3, 134.6, 134.0, 132.4, 132.1, 132.2, 128.5, 128.1, 127.6, 125.5, 117.8, 62.0 (CH$_2$), 50.7 (OC̲H$_3$), 42.4 (C–2), 40.3 (CH$_2$), 28.0 (C(C̲H$_3$)$_2$).
CHN: calc. C, 72.72; H, 5.84; N, 3.69, fnd C, 72.57; H, 5.78; N, 3.64.

b) Methyl 6-(4-Chlorophenyl)-2,3-dihydro-1-methoxy-2,2-dimethyl-7-phenyl-1H-pyrrolizin-5-yl]carboxylate Methyl 6-(4-chlorophenyl)-2,3-dihydro-2,2-dimethyl-7-phenyl-1H-pyrrolizin-5-yl]carboxylate (example 1a, 4.0 g (10.5 mmol) are reacted with 2.3 g (13.0 mmol) of NBS in CCl$_4$ to give methyl [1-bromo-6-(4-chlorophenyl)-2,3-dihydro-2,2-dimethyl-7-phenyl-1H-pyrrolizin-5-yl] carboxylate. The intermediate is not isolated, but reacted directly by addition of 30 ml of MeOH. After a few minutes, a solid deposits. The solvent is filtered off with suction and the solid is washed with a little methanol.

Yield: 3.5 g (81%), $C_{24}H_{24}ClNO_3$, 409.9 g/mol,
M.p.: 121° C.
IR (KBr): 1/l (cm$^{-1}$)=2981, 2956, 2900, 1698 (CO ester), 1455, 1438, 1312, 1217, 1135, 1083, 1012, 780, 703.
$^1$H-NMR (CDCl$_3$): d (ppm)=7.26–7.04 (m, 9H. 2Ar.), 4.19–4.14 (m, 3H, 1-H+3-H$_2$), 3.66 (s, 3H, COOCH$_3$), 3.07 (s, 3H, 1-OCH$_3$), 1.32 (s, 3H, 2-CH$_3$), 1.21 (e, 3H, 2-CH$_3$).
$^{13}$C-NMR (CDCl$_3$): d (ppm)=161.6 (C̲OOCH$_3$), 139.3, 134.5, 133.6, 132.4, 131.8, 132.2, 129.4, 128.1, 127.6, 126.0, 121.2, 116.2, 83.2 (C-1), 60.1 (C–3), 57.5 (OCH$_3$), 50.9 (COOC̲H$_3$), 46.7 (C–2), 27.2, 20.5 (C(C̲H$_3$)$_2$).
CHN: calc. C, 70.32; H, 5.90; N, 3.42, fnd C, 70.04; H, 5.70; N, 3.36.

EXAMPLE 2

6-(4-Chlorophenyl)-2,3-dihydro-1-methoxy-2,2-dimethyl-7-phenyl-1H-pyrrolizin-5-ylcarboxylic Acid Methyl 6-(4-chlorophenyl)-2,3-dihydro-1-methoxy-2,2-dimethyl-7-phenyl-1H-pyrrolizin-5-yl]carboxylate (example 1b, 3.5 g, 8.5 mmol) are heated to reflux for 16 h in a solution of 3.0 g (53.5 mmol) of KOH in 40 ml of MeOH. The mixture is then allowed to cool and is stirred into 400 ml of water, acidified to pH 3 with conc. HCl and extracted three times with 100 ml of diethyl ether each time. The ether extracts are washed with water and dried over Na$_2$SO$_4$. The solution is filtered and concentrated until the start of crystallization. The colorless solid is filtered off with suction and dried.

Yield: 2.9 g (86%), $C_{23}H_{22}ClNO_3$, 395.9 g/mol,
M.p.: 195° C.
IR (KBr): 1/l (cm$^{-1}$)=2958, 2895 (OH acid), 1650 (CO acid), 1516, 1492, 1469, 1316, 1136, 1107, 1091.
$^1$H-NMR ([D$_6$]-DMSO): d (ppm)=7.29–7.11 (m, 7H, Ph+AA'), 7.04–7.00 (BB', 2H), 4.26 (s, 1H, 1-H), 4.12 and 3.98 (m, 2H, AB system, 3-H$_2$, $^2$J=12.0 Hz), 2.97 (s, 3H, OCH$_3$), 1.22 (s, 3H, 2-CH$_3$), 1.14 (s, 3H, 2-CH$_3$).
$^{13}$C-NMR ([D$_6$]-DMSO): d (ppm)=161.6 (CO), 138.6, 134.3, 134.1, 131.1, 130.2, 132.5, 129.0, 128.1, 127.3, 125.9, 120.0, 116.5, 82.4 (C-1), 59.7 (C–3), 56.8 (OCH$_3$), 46.2 (C-2), 26.5, 20.3 (C(C̲H$_3$)$_2$).
CHN: calc. C, 69.78; H, 5.60; N, 3.54, fnd C, 69.58; H, 5.65; N, 3.45.

EXAMPLE 3

6-(4-Chlorophenyl)-2,3-dihydro-1-hydroxy-2,2-dimethyl-7-phenyl-1H-pyrrolizin-5-ylcarboxylic Acid 6-(4-Chlorophenyl)-2,3-dihydro-1-methoxy-2,2-dimethyl-7-phenyl-1H-pyrrolizin-5-yl]carboxylic acid (example 2, 0.50 g, 1.26 mmol) are dissolved in 10 ml of DMSO having a water content of about 10% and stirred at room temperature for 4 days after addition of 1.5 ml of conc. HCl. The mixture is then treated with 30 ml of water. The crystallizate is freed of the solvent by filtering off with suction and then taken up in 20 ml of diethyl ether. The organic phase is washed once with 20 ml of water and dried over Na$_2$SO$_4$. After filtration, the solvent is removed on a rotary evaporator. The solid residue is purified by recrystallizing from diethyl ether.

Yield: 0.10 g (21%), $C_{22}H_{20}ClNO_3$, 381.9 g/mol,
M.p.: 204° C.
IR (KBr): 1/l (cm$^{-1}$)=3510 (OH), 2954, 1639 (CO acid), 1468, 1313, 1139, 1102, 1091, 696.
$^1$H-NMR ([D$_6$]-DMSO): d (ppm)=7.33–7.05 (m, 9H, 2Ar.), 5.55 (d, 1H, OH, $^3$J=8.3 Hz), 4.30 (d, 1H, 1-H, $^3$J=8.3 Hz), 4.06 (m, 2H, 3-H$_2$), 1.17 (s, 3H, 2-CH$_3$), 1.02 (s, 3H, 2-CH$_3$).
$^{13}$C-NMR ([D$_6$]-DMSO): d (ppm)=161.7 (CO), 141.5, 134.5, 134.2, 131.1, 130.2, 132.5, 128.6, 128.0, 127.4, 125.5, 118.4, 116.0, 74.1 (C-1), 59.5 (C-3), 46.0 (C-2), 26.4, 20.6 (C(C̲H$_3$)$_2$).
CHN: calc. C, 69.20; H, 5.28; N, 3.67; fnd C, 68.70; H, 5.42; N, 3.51.

EXAMPLE 4

Methyl 6-(4-Chlorophenyl)-2,3-dihydro-1-oxo-2,2-dimethyl-7-phenyl-1H-pyrrolizin-5-ylcarboxylate
(129)

Methyl 6-(4-chlorophenyl)-2,3-dihydro-2,2-dimethyl-7-phenyl-1H-pyrrolizin-5-yl]carboxylate (example 1a, 8.0 g, 21.1 mmol) and 9.4 g (53 mmol) of NBS are heated under reflux for 3 h in 40 ml of CCl$_4$. 2.5 ml of water are then added and the mixture is refluxed for a further 16 h. The reaction mixture is concentrated to a residual volume of 5 ml and treated with 40 ml of MeOH. It is crystallized at 4° C. The pale solid is filtered off from the solvent with suction and dried in vacuo.

Yield: 4.36 g (53%), $C_{23}H_{20}ClNO_3$, 393.9 g/mol,

M.p.: 233° C.

IR (KBr): 1/l (cm$^{-1}$)=2976, 2872, 1707, 1699 (CO ester+ ketone), 1464, 1313, 1238, 1147, 1105, 692.

$^1$H-NMR (CDCl$_3$): d (ppm)=7.30–7.10 (m, 9H, 2Ar.), 4.46 (s, 2H, 3-H$_2$), 3.73 (s, 3H, OCH$_3$), 1.39 (8, 6H, 2-CH$_3$).

$^{13}$C-NMR (CDCl$_3$): d (ppm)=196.1 (CO), 160.9 (CO), 133.7, 133.3, 132.4, 131.0, 130.2, 132.1, 129.9, 128.0, 127.9, 127.3, 125.0, 122.0, 59.2 (C-3), 51.6 (OCH$_3$), 46.8 (C-2), 24.6 (C(CH$_3$)$_2$).

EXAMPLE 5

6-(4-Chlorophenyl)-2,3-dihydro-2,2-dimethyl-1-oxo-7-phenyl-1H-pyrrolizin-5-ylcarboxylic Acid Methyl 6-(4-chlorophenyl)-2,3-dihydro-1-oxo-2,2-dimethyl-7-phenyl-1H-pyrrolizin-5-ylcarboxylate (example 4, 4.4 g, 11.1 mmol) is heated to reflux for 2 h in a solution of 3.0 g (53.5 mmol) of KOH in 40 ml of MeOH. The mixture is then allowed to cool and is stirred into 600 ml of water. The cloudy solution is brought to pH 3 using concentrated hydrochloric acid. The precipitate [lacuna] separated off by filtration and dried over phosphorus pentaoxide in a vacuum desiccator.

Yield: 3.8 g (90%), $C_{22}H_{18}ClNO_3$, 379.9 g/mol,

M.p.: 284° C.

IR (KBr): 1/l (cm$^{-1}$)=2970, 1707 (CO ketone), 1656 (CO acid), 1518, 1476, 1316, 1302, 1148, 1101, 699.

$^1$H-NMR ([D$_6$]-DMSO): d (ppm)=7.35–7.31 (AA', 2H), 7.20–7.10 (m, 7H, Ph+BB'), 4.45 (s, 2H, CH$_2$), 1.26 (s, 6H, 2-CH$_3$).

$^{13}$C-NMR ([D$_6$]-DMSO): d (ppm)=196.1 (C-1), 161.0 (COOH), 132.9, 132.3, 131.8, 131.3, 132.4, 129.6, 127.8, 127.6, 127.0, 129.2, 123.4, 122.9, 58.5 (C-3), 48.3 (C-2), 24.1 (C(CH$_3$)$_2$).

CHN: calc. C, 69.56; H, 4.78; N, 3.69; fnd C, 69.06; H, 4.81; N, 3.53.

EXAMPLE 6

6-(4-Chlorophenyl)-2,3-dihydro-2,2-dimethyl-1-oxo-7-phenyl-1H-pyrrolizine 6-(4-Chlorophenyl)-2,3-dihydro-2,2-dimethyl-1-oxo-7-phenyl-1H-pyrrolizin-5-ylcarboxylic acid (example 5, 2.0 g, 5.3 mmol) are heated to a melt for 10 min (about 290° C.). As soon as the evolution of gas is complete, the mixture is allowed to cool and the melt cake is treated in an ultrasonic bath with MeOH (30 min). The solvent is then filtered off with suction and the pale brown solid is dried.

Yield: 1.31 g (74%), $C_{21}H_{18}ClNO$, 335.8 g/mol,

M.p. 261° C.

IR (KBr): 1/l (cm$^{-1}$)=3116 (CH), 2970 (CH), 1684 (CO ketone), 1529, 1350, 1092, 1016, 821, 698, 534.

$^1$H-NMR (CDCl$_3$): d (ppm)=7.47–7.10 (m, 9H, 2Ar.), 7.09 (s, 1H, 5-H), 4.14 (s, 2H, 3-H$_2$), 1.37 (s, 6H, 2-CH$_3$).

$^{13}$C-NMR (CDCl$_3$): d (ppm)=194.6 (CO), 133.3, 132.5, 132.0, 129.9, 123.8, 130.0, 129.8, 128.6, 128.1, 127.8, 121.9, 56.8 (C-3), 49.7 (C-2), 24.8 (C(CH$_3$)$_2$).

CHN: calc. C, 75.11; H, 5.40; N, 4.17; fnd C, 73.51; H, 5.27; N, 4.09.

EXAMPLE 7

6-(4-Chlorophenyl)-2,3-dihydro-1-hydroxy-2,2-dimethyl-7-phenyl-1H-pyrrolizine 6-(4-Chlorophenyl)-2,3-dihydro-2,2-dimethyl-1-oxo-7-phenyl-1H-pyrrolizine (example 6, 0.30 g, 0.9 mmol) are suspended in THF. 0.04 g (1.1 mmol) of LiAlH$_4$ is added and the mixture is heated to reflux for 0.5 h. It is then allowed to cool and excess hydride is decomposed by addition of 10 ml of saturated NaHCO$_3$ solution. 10 ml of 10 percent NaOH is then added and the organic phase is separated off. The aqueous phase is extracted a further three times with 10 ml of diethyl ether. The organic extracts are dried over Na$_2$SO$_4$, filtered and concentrated in a rotary evaporator. The product foams in vacuo. It is freed of residual solvent in vacuo at 40° C.

Yield: 0.28 g (96%), $C_{21}H_{20}ClNO$, 337.9 g/mol

IR (KBr): 1/l (cm$^{-1}$)=3336 (b), 2958, 2870, 1601, 1525, 1486, 1409, 1173, 1092, 1032, 1012, 833, 767, 700.

$^1$H-NMR (CDCl$_3$): d (ppm)=7.35–7.12 (m, 9H, 2Ar.), 6.71 (s, 1H, 5-H), 4.55 (d, 1H, 1-H, $^3$J=5.3 Hz), 3.96 and 3.64 (AB, 2H, 3-H$_2$, $^2$J=10.5 Hz), 1.76 (d, 1H, 1-OH, $^3$J=5.5 Hz), 1.30 (s, 3H, 2-CH$_3$), 1.14 (s, 3H, 2-CH$_3$).

$^{13}$C-NMR (CDCl$_3$): d (ppm)=136.9, 135.1, 134.7, 131.2, 129.6, 128.9, 128.28, 128.26, 125.6, 125.7, 117.3, 114.4 (C-5), 75.4 (C-1), 57.5 (C-3), 47.8 (C-2), 26.6, 20.8 (C(CH$_3$)$_2$).

CHN: calc. C, 74.67; H, 5.97; N, 4.15; fnd C, 74.06; H, 5.99; N, 3.97.

EXAMPLE 8

6-(4-Chlorophenyl)-2,3-dihydro-2,2-dimethyl-1-oxo-7-phenyl-1H-pyrrolizin-5-ylcarbaldehyde 6-(4-Chlorophenyl)-2,3-dihydro-2,2-dimethyl-1-oxo-7-phenyl-1H-pyrrolizine (example 6, 0.30 g (0.9 mmol) are suspended in 1 ml of DMF. The suspension is cooled to 5° C.; 0.28 g (1.8 mmol) of POCl$_3$ is then added. It is stirred at room temperature for 30 min and then heated at 80° C. for 16 h. The cooled reaction mixture is hydrolyzed using 10 ml of 10% sodium hydroxide solution and extracted twice with 20 ml of methylene chloride. The organic extracts are washed three times with 40 ml of water, dried over Na$_2$SO$_4$ filtered and concentrated in a rotary evaporator. The crude product is recrystallized from ethanol.

Yield: 250 mg (76%), $C_{22}H_{18}ClNO_2$, 363.8 g/mol,

M.p. 185° C.

IR (KBr): 1/l (cm$^{-1}$)=2962, 2868, 1716 (CO aldehyde), 1662 (CO ketone), 1514, 1458, 1406, 1381, 1118, 1014, 845, 746, 723.

$^1$H-NMR (CDCl$_3$): d (ppm)=9.64 (8, 1H, CHO), 7.38–7.19 (m, 9H, 2Ar.), 4.49 (s, 2H, 3-H2), 1.39 (s, 6H, 2-CH$_3$).

$^{13}$C-NMR (CDCl$_3$): d (ppm)=196.9 (CO), 181.7 (CHO), 136.8, 134.3, 130.5, 130.3, 129.3, 124.1, 131.9, 129.7, 128.9, 128.2, 127.6, 58.6 (C-3), 49.2 (C-2), 24.6 (C(CH$_3$)$_2$).

CHN: calc. C, 72.63; H, 4.99; N, 3.85; fnd C, 72.34; H, 5.22; N, 3.80.

EXAMPLE 9 tert-Butyl 1-Acetoxy-6-(4-chorophenyl)-2,3-dihydro-2,2-dimethyl-7-phenyl-1H-pyrrolizin-5-ylacetate a) tert-Butyl 6-(4-Chlorophenyl)-2,3-dihydro-2,2-dimethyl-7-phenyl-1H-pyrrolizin-5-ylacetate 6-(4-Chlorophenyl)-2,3-dihydro-1-hydroxy-2,2-dimethyl-7-phenyl-1H-pyrrolizin-5-yl]acetic acid (ML3000, 10.0 g, 26.3 mmol), prepared according to Laufer et al.(J. Med. Chem. 1994, 37, 1894–1897), are dissolved in 40 ml of absolute THF and treated with 5.1 g is (31.5 mmol) of carbonyldiimidazole. The mixture is stirred for 30 min until the imidazolide precipitates at room temperature, then 80 ml of tert-butanol are added and the mixture is heated to 100° C. on a water separator. As soon as the THF has completely distilled over, the reaction mixture is heated at 110° C. for a further 7 days. It is then allowed to cool and is stirred with 80 ml of diethyl ether or MeOH. The crystallizate is freed of the solvent by filtering off with suction and dried. Further crystallizate can be obtained from the mother liquor by concentrating in a rotary evaporator and precipitating with MeOH.

Yield: 8.0 g (70%), $C_{27}H_{30}ClNO_2$ 436.0 g/mol,
M.p.: 168° C.

IR (KBr): 1/l (cm$^{-1}$)=2954, 2870, 1728 (CO ester), 1487, 1379, 1163, 1151, 1097, 822, 700. $^1$H-NMR (CDCl$_3$): d (ppm) 7.27–7.03 (m, 9H, 2Ar.), 3.75 (s, 2H, CH$_2$), 3.41 (s, 2H, CH$_2$), 2.84 (s, 2H, CH$_2$), 1.47 (s, 9H, (CCH$_3$)$_3$), 1.29 (s, 6H, 2-CH$_3$).

$^{13}$C-NMR (CDCl$_3$): d (ppm)=170.1 (CO), 136.1, 134.8, 133.9, 131.5, 131.6, 128.2, 128.1, 128.0, 124.6, 118.4, 114.6, 81.2 (OC(CH$_3$)$_3$), 58.3 (CH$_2$), 43.3 (C-2), 40.5 (CH$_2$), 32.9 (CH$_2$), 28.1 (OC(CH$_3$)$_3$), 35 28.0 (C(CH$_3$)$_2$).

CHN: calc. C, 74.38; H, 6.94; N, 3.21; fnd C, 73.99; H, 6.90; N, 3.21.

b) tert-Butyl 1-Bromo-6-(4-chlorophenyl)-2,3-dihydro-2,2-dimethyl-7-phenyl-1H-pyrrolizin-5-ylacetate tert-Butyl 6-(4-chlorophenyl)-2,3-dihydro-2,2-dimethyl-7-phenyl-1H-pyrrolizin-5-ylacetate (example 9a, 5.0 g, 11.5 mmol) and NBS (2.2 g, 12.4 mmol) are treated with 50 ml of CCl$_4$ and a spatula-tipful of AIBN. The reaction mixture is heated at 50° C. for 45 min. After cooling, the succinimide is separated off by filtration and the solvent is removed in vacuo.

Yield: 5.6 g (95%), $C_{27}H_{29}BrClNO_2$; 514.9 g/mol.

IR (KBr): 1/l (cm−1)=2968, 2931 (s, aliphat. CH), 1730 (s, broad, CO, ester), 1466, 1367, 1147, 1099, 833, 787, 770 (s, C—Br).

$^1$H-NMR (CDCl$_3$): d (ppm)=7.30–7.12 (m, 7H, Ph+AA'), 7.11–7.06 (BB', 2H), 5.15 (s, 1H, 1-H), 3.81 (s, broad, 2H, 3-H$_2$), 3.41 (s, 2H, CH$_2$COOR), 1.48 (s, 9H, C(CH$_3$)$_3$), 1.35 (s, broad, 6 H, 2CH$_3$).

$^{13}$C-NMR (CDCl$_3$): d (ppm)=169.5 (CO), 134.8, 133.9, 133.5, 132.0, 131.7, 128.9, 128.3, 128.1, 125.6, 124.3, 121.7, 118.0, 81.6 (OC(CH$_3$)$_3$), 60.8 (C-1), 55.4 (CH$_2$), 49.4 (C-3), 32.9 (CH$_2$), 28.8 (OC(CH$_3$)$_3$), 25.9 (C(CH$_3$)$_2$).

c) tert-Butyl 1-Acetoxy-6-(4-chlorophenyl)-2,3-dihydro-2, 2-dimethyl-7-phenyl-1-pyrrolizin-5-ylacetate tert-Butyl 1-bromo-6-(4-chlorophenyl)-2,3-dihydro-2,2-dimethyl-7-phenyl-1H-pyrrolizin-5-ylacetate (example 9b, 1.15 g, 2.23 mmol) is treated with 0.5 g of potassium acetate, 10 ml of absolute diethyl ether and 3 drops of acetic acid and the mixture is heated under reflux for 3 h. It is then allowed to cool, the inorganic salts are filtered off and the ether solution is concentrated in a rotary evaporator. At a residual volume of about 5 ml, 10 ml of hexane are added. After triturating, the product precipitates and is separated off by filtering off the solvent with suction.

Yield 0.74 g (65%) $C_{29}H_{32}ClNO_4$; 494.0 g/mol,
M.p.: 81° C.

IR (KBr): 1/l (cm$^{-1}$) 2972, 1728 (CO ester), 1368, 1246, 1149, 1014, 833, 708.

$^1$H-NMR (CDCl$_3$): d (ppm)=7.24–6.99 (m, 9H, 2.Ar.), 5.92 (s, 1H, 1-H), 3.92 and 3.75 (2H, AB, 3-H2, $^2$J=10.4 Hz), 3.43 (s, 2H, CH$_2$COOR), 2.09 (s, 3H, OCH$_3$), 1.48 (s, 9H, OC(CH$_3$)$_3$), 1.25 (s, 3H, 2-CH$_3$), 1.21 (s, 3H, 2-CH$_3$).

$^{13}$C-NMR (CDCl$_3$): d (ppm)=170.3 (CO), 169.7 (CO), 134.7, 134.1, 131.8, 130.8, 131.7, 128.6, 128.2, 128.0, 125.5, 124.3, 120.1, 118.6, 81.5, (OC(CH$_3$)$_3$), 76.3 (C-1), 56.5 (C-3), 47.6 (C-2), 32.8 (CH$_2$COOR), 28.1 (OC(CH$_3$)$_3$), 26.6 (OCH$_3$), 21.0, 20.9 (CH$_3$).

CHN: calc. C, 70.50; H, 6.53; N, 2.84; fnd C, 70.83; H, 6.71; N, 2.81.

EXAMPLE 10

Ethyl 1-Acetoxy-6-(4-chlorophenyl)-2,3-dihydro-2, 2-dimethyl-7-phenyl-1H-pyrrolizin-5-yl]-2-oxoacetate a) Ethyl 1-Bromo-6-(4-chlorophenyl)-2,3-dihydro-2,2-dimethyl-7-phenyl-1H-pyrrolizin-5-yl-2-oxoacetate Ethyl 6-(4-chlorophenyl)-2,3-dihydro-2,2-dimethyl-7-phenyl-1H-pyrrolizin-5-yl]-2-oxoacetate (9.82 g, 23.3 mmol), prepared according to the literature, are dissolved in 50 ml of CCl$_4$. 4.70 g (26.4 mmol) of NBS and a spatula-tipful of azoisobutyronitrile (AIBN) are then added and the mixture is heated to reflux for 4 h. After the reaction mixture has cooled, the succinimide is filtered off and the clear solution is concentrated in a rotary evaporator. The residue crystallizes from diisopropyl ether.

Yield: 8.9 g (76%), $C_{25}H_{23}BrClNO_3$, 500.8 g/mol.
M.p. 167° C.

IR (KBr): 1/l (cm$^{-1}$)=2966 (CH), 1740 (CO ester), 1630 (CO a-ketone), 1446, 1433, 1257, 1068, 1018, 851, 696.

$^1$H-NMR (CDCl$_3$): d (ppm)=7.30–7.13 (m, 9H, 2Ar.), 5.00 (s, 1H, 1-H), 4.34 and 4.14 (2H, AB, 3-CH$_2$, $^2$J=12.5 Hz), 3.64 (m, 2H, ABX$_3$, OCH$_2$, $^2$J=10.8 Hz, $^3$J=7.3 Hz), 1.51 (s, 3H, 2-CH$_3$), 1.28 (s, 3H, 2-CH$_3$), 1.08 (t, 3H, OCH$_2$CH$_3$, $^3$J=7.2 Hz).

$^{13}$C-NMR (CDCl$_3$): d (ppm)=177.4, 164.1 (CO), 143.3, 135.4, 134.0, 132.4, 131.7, 132.2, 129.0, 128.3, 128.2, 126.8, 122.9, 120.5, 61.9 (CH$_2$), 59.0 (CH$_2$), 54.9 (C-1), 48.3 (C-2), 26.4, 24.9 (C(CH$_3$)$_2$), 13.5 (OCH$_2$CH$_3$).

CHN: calc. C, 59.96; H, 4.63; N, 2.80; fnd C, 59.95; H, 4.64; N, 2.74.

b) Ethyl 1-Acetoxy-6-(4-chlorophenyl)-2,3-dihydro-2,2-dimethyl-7-phenyl-1H-pyrrolizin-5-yl-2-oxoacetate Ethyl 1-bromo-6-(4-chlorophenyl)-2,3-dihydro-2,2-dimethyl-7-phenyl-1H-pyrrolizin-5-yl-2-oxoacetate (example 10a, 10.0 g, 20 mmol) are dissolved in 50 ml of DMF. After the addition of potassium acetate (5.0 g, 51 mmol), the mixture is heated at 80° C. for 2 h. The cooled reaction mixture is poured onto ice and extracted with 200 ml of diethyl ether. The ether phase is separated off, washed twice with 150 ml of water, dried over Na$_2$SO$_4$ filtered and concentrated in a rotary evaporator. A mixture of ethyl 1-acetoxy-6-(4-chlorophenyl)-2,3-dihydro-2, 2-dimethyl-7-phenyl-1H-pyrrolizin-5-yl-2-oxoacetate and ethyl 2-(6-(4-chlorophenyl)-2,3-dihydro-1-hydroxy-2,2-dimethyl-7-phenyl-1H-pyrrolizin-5-yl-2-oxoacetate is obtained.

Yield : 6.9 g (75%) of a mixture containing various proportions of the two components). Separation of the components by means of column chromatography (silica gel 60, ether/cyclohexane 1:1) yields: ethyl 2-[1-acetoxy-6-(4-chlorophenyl)-2,3-dihydro-2,2-dimethyl-7-phenyl-1H-pyrrolizin-5-yl-2-oxoacetate $C_{27}H_{26}ClNO_5$, 480.0 g/mol:

M.p.: 142° C.;

IR (KBr): 1/l (cm$^{-1}$)=2970 (CH), 1747 (CO ester), 1624 (CO a-ketone), 1448, 1427, 1227, 1084, 1018, 733, 696.

$^1$H-NMR (CDCl$_3$): d (ppm)=7.29–6.91 (m, 9H, 2Ar.), 5.95 (s, 1H, 1-H), 4.32 and 4.24 (2H, AB, 3-H$_2$, $^2$J=12.4 Hz), 3.70–3.55 (m, 2H, ABX$_3$, OCH$_2$), 2.03 (s, 3H, OCH$_3$), 1.30 (s, 3H, 2-CH$_3$), 1.22 (s, 3H, 2-CH$_3$), 1.07 (t, 3H, OCH$_2$CH$_3$, $^3$J=7.1 Hz).

$^{13}$C-NMR (CDCl$_3$): d (ppm)=177.4 (CO a-ketone), 169.8 (CO), 164.1 (CO), 140.8, 135.5, 133.9, 132.3, 131.8, 128.9, 128.3, 121.3, 132.1, 128.8, 128.2, 128.1, 126.7, 75.0 (C-1), 61.8 (CH$_2$), 60.4 (CH$_2$), 46.7 (C-2), 26.4 (CO$\underline{C}$H$_3$), 20.8, 20.6 (CH$_3$), 13.5 (OCH$_2\underline{C}$H$_3$).

CHN: calc. C, 67.57; H, 5.46; N, 2.92; fnd C, 67.48; H, 5.48; N, 2.89.

EXAMPLE 11

Ethyl 6-(4-Chlorophenyl)-2,3-dihydro-1-hydroxy-2, 2-dimethyl-7-phenyl-1H-pyrrolizin-5-yl-2-oxoacetate After column chromatography from example 10b: C$_{25}$H$_{24}$ClNO$_4$, 438.0 g/mol.

M.p.: 193° C.

IR (KBr): 1/1 (cm$^{-1}$)=3520 (OH), 2958 (CH), 1730 (CO ester), 1622 (CO a-ketone), 1450, 1425, 1269, 1076, 1016, 737, 700.

$^1$H-NMR (CDCl$_3$): d (ppm)=7.29–7.12 (m, 9H, 2Ar.), 4.64 (d, 1H, 1-H, $^3$J=5.8 Hz), 4.29 and 4.23 (2H, AB, 3-H$_2$, $^2$J=9.8 Hz), 3.75–3.50 (m, 2H, ABX$_3$, OCH$_2$), 1.96 (d, 1H, OH, $^3$J=5.8 Hz), 1.32 (s, 3H, 2-CH$_3$), 1.20 (s, 3H, 2-CH$_3$), 1.07 (t, 3H, OCH$_2\underline{C}$H$_3$, $^3$J=7.2 Hz).

$^{13}$C-NMR (CDCl$_3$): d (ppm)=177.5 ($\underline{C}$O a-ketone), 164.3 ($\underline{C}$O ester), 144.6, 135.5, 133.9, 132.8, 132.0, 132.2, 129.0, 128.4, 128.2, 126.6, 122.0, 120.8, 75.1 (C-1), 61.8 (CH$_2$), 60.0 (CH$_2$), 46.9 (C-2), 26.4 (C($\underline{C}$H$_3$)$_2$), 20.5 (C($\underline{C}$H$_3$)$_2$), 13.5 (OCH$_2\underline{C}$H$_3$).

EXAMPLE 12

6-(4-Chlorophenyl)-2,3-dihydro-1-hydroxy-2,2-dimethyl-7-phenyl-1H-pyrrolizin-5-ylacetic Acid tert-Butyl 1-acetoxy-6-(4-chlorophenyl)-2,3-dihydro-2,2-dimethyl-7-phenyl-1H-pyrrolizin-5-ylacetate (example 9c, 1.00 g, 2.0 mmol) is dissolved in 10 ml of MeOH. 0.5 g of KOH is added and the mixture is heated under reflux until the intermediately formed precipitate has dissolved. It is then allowed to cool and is stirred into 600 ml of water. The cloudy solution is brought to pH 3 using conc. HCl. It is extracted three times using 100 ml of diethyl ether each time. The ether extracts are washed twice with water and dried over Na$_2$SO$_4$, filtered and concentrated in a rotary evaporator. A mixture of 6-(4-chlorophenyl)-2,3-dihydro-1-hydroxy-2,2-dimethyl-7-phenyl-1H-pyrrolizin-5-ylacetic acid and 2-[6-(4-chlorophenyl)-2,3-dihydro-1-methoxy-2,2-dimethyl -7-phenyl-1H-pyrrolizin-5-yl]acetic acid is obtained (cf. example 16).

Alternative synthesis of (6-(4-chlorophenyl)-2,3-dihydro-1-hydroxy-2,2-dimethyl-7-phenyl-1H-pyrrolizin-5-ylacetic acid) A product mixture which contains a 1:2 mixture of ethyl 2-[1-acetoxy-6-(4-chlorophenyl)-2,3-dihydro-2,2-dimethyl-7-phenyl-1H-pyrrolizin-5-yl]-2-oxoacetate and ethyl 2-[6-(4-chlorophenyl)-2,3-dihydro-1-hydroxy-2,2-dimethyl-7-phenyl-1H-pyrrolizin-5-yl]-2-oxo-acetate (from example 10b, 1.50 g, 3.31 mmol) is suspended in 15 ml of diethylene glycol, treated with 1.3 ml of hydrazine hydrate (80 percent) and heated at 80° C. for 1 h. It is then allowed to cool and 2.5 g of KOH are added. It is then heated at 130° C. for 1 h and at 160° C. for 2 h. After cooling, it is diluted with 30 ml of water and brought to pH 2 using conc. HCl and extracted three times with 30 ml of diethyl ether. The organic extracts are washed twice with 50 ml of water, dried over Na$_2$SO$_4$ filtered and concentrated to a residual volume of 50 ml in a rotary evaporator. About 20 ml of hexane are then added and the mixture is evaporated until the start of crystallization. The crystallizate is separated off by filtering off with suction, and the solution is further concentrated. A number of crystallizate fractions are obtained in this way. The last crystallizates contain the compound sought.

Yield: 0.07 g (6%) C$_{23}$H$_{22}$ClNO$_3$, 395.9 g/mol.

IR (KBr): 1/1 (cm$^{-1}$)=3421 (OH), 2958, 2926, 2870 (OH), 1730 (CO acid), 1485, 1090, 1012, 831, 700.

$^1$H-NMR (CDCl$_3$): d (ppm)=7.28–7.06 (m, 9H, 2Ar.), 4.61 (s, 1H, 1-H), 3.91, 3.68 (2H, AB, 3-H$_2$, $^2$J=10.4 Hz), 3.58 (2H, AB, C$\underline{H}_2$COOH), 1.31 (s, 3H, 2-CH$_3$), 1.15 (s, 3H, 2-CH$_3$).

EXAMPLE 13 tert-Butyl 6-(4-Chlorophenyl)-2,3-dihydro-1-methoxy-2,2-dimethyl-7-phenyl-1H-pyrrolizin-5-ylacetate tert-Butyl 1-bromo-6-(4-chlorophenyl)-2,3-dihydro-2,2-dimethyl-7-phenyl-1H-pyrrolizin-5-yl]acetate (example 9b, 1.15 g, 2.23 mmol) are dissolved in 10 ml of MeOH. After a few minutes, a solid deposits. The solvent is filtered off with suction and the solid is washed with a little MeOH.

Yield: 0.73 g (70%), C$_{28}$H$_{32}$ClNO$_3$, 466.0 g/mol,

M.p.: 140° C.

IR (KBr): 1/1 (cm$^{-1}$)=2881, 1728 (CO ester), 1153, 1369, 1342, 1214, 1089, 827, 746, 698. $^1$H-NMR (CDCl$_3$): d (ppm)=7.25–7.08 (m, 9H, 2Ar.), 4.22 (s, 1H, 1-H), 3.88, 3.65 (2H, AB, 3-H$_2$, $^2$J=10.3 Hz), 3.43 (s, 2H, C$\underline{H}_2$COOR), 3.09 (s, 3H, OCH$_3$), 1.45 (s, 9H, OC(CH$_3$)$_3$), 1.32 (3, 3H, 2-CH$_3$), 1.20 (s, 3H, 2-CH$_3$).

$^{13}$C-NMR (CDCl$_3$): d (ppm)=169.7 ($\underline{C}$O), 135.9, 134.5, 133.3, 131.5, 131.7, 129.1, 128.1, 128.0, 125.3, 123.7, 119.3, 118.9, 83.5 (C-1), 81.3 (OC(CH$_3$)$_3$), 56.8 (O$\underline{C}$H$_3$), 56.4 (C-3), 47.7 (C-2), 32.9 ($\underline{C}$H$_2$COOR), 28.0 (OC(CH$_3$)$_3$), 27.3, 20.8 (C(CH$_3$)$_2$).

CHN: calc. C, 72.17; H, 6.92; N, 3.01, fnd C, 71.38; H, 6.85; N, 2.99.

EXAMPLE 14

6-(4-Chlorophenyl)-2,3-dihydro-1-methoxy-2,2-dimethyl-7-phenyl-1H-pyrrolizin-5-ylacetic Acid tert-Butyl 6-(4-chlorophenyl)-2,3-dihydro-1-methoxy-2, 2-dimethyl-7-phenyl-1H-pyrrolizin-5-ylacetate (example 13, 1.00 g, 2.14 mmol) is suspended in 10 ml of MeOH. 0.5 g of KOH is added and the mixture is heated to reflux for 2 h. It is then allowed to cool and is stirred into 600 ml of water. The cloudy solution is brought to pH 3 using conc. HCl. It is extracted three times with 100 ml each of diethyl ether. The ether extracts are washed twice with water and dried over Na$_2$SO$_4$. The solution is filtered and concentrated in a rotary evaporator until the start of crystallization. The colorless solid is freed of the residual solvent by filtering off with suction and dried.

Yield: 0.66 g (75%), C$_{24}$H$_{24}$ClNO$_3$, 409.9 g/mol,

M.p.: 168° C.

IR (KBr): 1/1 (cm$^{-1}$)=3034 (CH), 2966, 2884 (OH), 1716 (CO acid), 1092, 1456, 1225, 1206, 1016, 697.

$^1$H-NMR ([D$_6$]-DMSO): d (ppm)=7.34–7.28 (m, 2H, AA'), 7.25–7.02 (m, 7H, Ph+BB'), 4.23 (8, 1H, 1-H), 3.71 (s, 2H, C$\underline{H}_2$COOH), 3.55 and 3.41 (2H, AB, 3-H$_2$, $^2$J=16.8 Hz), 2.92 (s, 3H, OCH$_3$), 1.21 (s, 3H, 2-CH$_3$), 1.12 (s, 3H, 2-CH$_3$).

$^{13}$C-NMR (CDCl$_3$/[D$_6$]-DMSO): d (ppm)=172.4 (CO), 135.9, 134.4, 133.4, 131.2, 131.6, 129.0, 128.0, 127.96, 125.2, 123.3, 119.3, 118.6, 83.4 (C-1), 56.9 (OCH$_3$), 56.4 (C-3), 47.5 (C-2), 31.4 (CH$_2$COOH), 27.3, 20.8 (C(CH$_3$)$_3$).

CHN: calc. C, 70.33; H, 5.90; N, 3.42; fnd C, 69.67; H, 5.90; N, 3.36.

EXAMPLE 15

6-(4-Chlorophenyl)-2,3-dihydro-1-hydroxy-2,2,5-trimethyl-7-phenyl-1H-pyrrolizine 6-(4-Chlorophenyl)-2,3-dihydro-1-methoxy-2,2-dimethyl-7-phenyl-1H-pyrrolizin-5-ylacetic acid (example 14, 0.50 g, 1.22 mmol) is suspended in a mixture of 5 ml of DMSO and 1 ml of water and heated at 90–100° C. for 4 h. After cooling the reaction mixture, 30 ml of diethyl ether are added, the aqueous phase is separated off and the ether solution is washed three times with 50 ml of water. After drying over Na$_2$SO$_4$ and filtration, the solution is concentrated in vacuo. The residue is crystallized from cyclohexane.

Yield: 0.26 g (60%), C$_{22}$H$_{22}$ClNO, 351.9 g/mol,

M.p.: 133° C.

IR (KBr): 1/l (cm$^{-1}$)=3302 (OH), 2956, 2906, 1486, 1381, 1054, 999, 831, 732, 699.

$^1$H-NMR (CDCl$_3$): d (ppm)=7.26–7.11 (m, 7H, Ph+AA'), 7.09–7.05 (2H, BB'), 4.57 (d, 1H, 1-H, $^3$J=5.1 Hz), 3.84 and 3.59 (2 H, AB, 3-H$_2$, $^2$J=10.4 Hz), 2.19 (s, 3H. 5-CH$_3$), 1.74 (d, 1H, OH, $^3$J=5.1 Hz), 1.31 (s, 3H, 2-CH$_3$), 1.15 (s, 3H, 2-CH$_3$).

$^{13}$C-NMR ([D$_6$]-DMSO): d (ppm)=136.0, 135.7, 135.3, 130.0, 131.6, 128.3, 128.2, 128.1, 124.8, 121.6, 120.3, 115.8, 74.8 (C-1), 55.3 (C-3), 47.0 (C-2), 26.9 (C(CH$_3$)$_2$), 21.2 (C(CH$_3$)$_2$), 10.4 (CH$_3$-5).

MS (ES$^+$, 35 V), m/z (% rel. Int.), 352 (11, (M+H)$^+$), 334 (100).

CHN: calc. C, 75.09; H, 6.30; N, 3.98; fnd C, 75.21; H, 6.37; N, 4.18.

EXAMPLE 16

6-(4-Chlorophenyl)-2, 3-dihydro-1-methoxy-2,2,5-trimethyl-7-phenyl-1H-pyrrolizine 6-(4-Chlorophenyl)-2,3-dihydro-1-hydroxy-2,2,5-trimethyl-7-phenyl-1H-pyrrolizine (example 15, 0.38 g, 1.08 mmol) is dissolved in 10 ml of MeOH. The clear solution is treated briefly with HCl gas until a pale precipitate deposits. It is then diluted with 10 ml of MeOH and the solid is separated off by filtering off the solvent with suction. It is additionally washed a number of times with MeOH and allowed to dry in the air.

Yield: 0.30 g (76w), C$_{23}$H$_{24}$ClNO, 365.9 g/mol,

M.p.: 179° C.

IR (KBr): 1/l (cm$^{-1}$) 2980, 2935, 2878, 1484, 1463, 1380, 1317, 1181, 1087, 819, 766, 750, 696.

$^1$H-NMR (CDCl$_3$): d (ppm)=7.25–7.11 (m, 7H, Ph+AA'), 7.07–7.02 (2H, BB'), 4.20 (s, 1H, 1-H), 3.82 and 3.55 (2H, AB, 3-H$_2$), 3.03 (s, 3H, OCH$_3$), 2.20 (s, 3H, 5-CH$_3$), 1.31 (s, 3H, 2-CH$_3$), 1.21 (s, 3H, 2-CH$_3$).

$^{13}$C-NMR (CDCl$_3$): d (ppm)=136.3, 135.1, 132.1, 130.9, 131.5, 129.1, 128.0, 125.2, 122.2, 121.5, 118.8, 83.5 (C-1), 56.8 (OCH$_3$), 55.9 (C-3), 47.4 (C-2), 27.5, 20.9 (C(CH$_3$)$_2$), 10.7 (CH$_3$-5)

CHN: calc. C, 75.48; H, 6.61; N, 3.83; fnd C, 75.05; H, 6.55; N, 3.80.

EXAMPLE 17 tert-Butyl 6-(4-Chlorophenyl)-2,3-dihydro-2,2-dimethyl-1-oxo-7-phenyl-1H-pyrrolizin-5-yl]acetate tert-Butyl 6-(4-chlorophenyl)-2,3-dihydro-2,2-dimethyl-7-phenyl-1H-pyrrolizin-5-ylacetate (example 9a, 15.0 g, 34.4 mmol) and NBS (13.5 9, 75.8 mmol) are suspended in 75 ml of CCl$_4$. 5 ml of water are added and the mixture is heated at 70° C. for 2.5 h. The cooled reaction mixture is dried over Na$_2$SO$_4$, filtered and the solvent is removed on a rotary evaporator. The residue crystallizes at 5° C. from MeOH. The solvent is filtered off with suction and the crystallizate is washed with ice-cold MeOH.

Yield: 9.0 g (58%). C$_{27}$H$_{28}$ClNO$_3$; 450.0 g/mol,

M.p.: 180° C.

IR (KBr): 1/l (cm$^{-1}$) 1728 (CO ester), 1686 (CO ketone), 1541, 1365, 1294, 1144, 1095, 1014, 833, 694.

$^1$H-NMR (CDCl$_3$): d (ppm)=7.40–7.36 (AA', 2H), 7.32–7.19 (m, 5H, Ph), 7.14–7.09 (BB', 2H), 4.10 (s, 2H, CH$_2$), 3.50 (s, 2H, CH$_2$), 1.47 (s, 9H, OC(CH$_3$)$_3$,), 1.38 (s, 6H, 2-CH$_3$).

$^{13}$C-NMR (CDCl$_3$): d (ppm)=194.3 (CO), 168.3 (CO), 133.0, 132.8, 132.1, 131.7, 129.7, 128.7, 127.9, 127.0, 128.5, 127.5, 124.7, 82.2 (OC(CH$_3$)$_3$), 55.4 (CH$_2$), 49.6 (C-2), 32.5 (C-3), 28.0 (OC(CH$_3$)$_3$), 24.9 (C(CH$_3$)$_2$).

CHN: calc. C, 72.07; H, 6.27; N, 3.11; fnd C, 71.29; H, 6.27; N, 2.97.

EXAMPLE 18

6-(4-Chlorophenyl)-2,3-dihydro-2,2-dimethyl-1-oxo-7-phenyl-1H-pyrrolizin-5-ylacetic Acid tert-Butyl 6-(4-chlorophenyl)-2,3-dihydro-2,2-dimethyl-1-oxo-7-phenyl-1H-pyrrolizin-5-yl]acetate (example 17, 14.0 g, 31.1 mmol) is added to a solution of 15.0 g of KOH in 180 ml of MeOH and the mixture is heated to reflux for 2 h, allowed to cool and stirred into 600 ml of water. The solution is brought to pH 3 using conc. HCl and extracted with 100 ml each of diethyl ether. The ether extracts are washed with water and dried over sodium sulfate. The solution is filtered and the volume is reduced in vacuo until the start of crystallization. The solid is collected and dried.

Yield: 10.6 g (86%), C$_{23}$H$_{20}$ClNO$_3$; 393.9 g/mol,

M.p.: 234.3° C.

IR (KBr): 1/l (cm$^{-1}$)=2968, 2926 (CH), 1743 (CO acid), 1650 (CO ketone), 1534, 1364, 1330, 1172, 1107, 696.

$^1$H-NMR ([D$_6$]-DMSO) d (ppm)=7.43–7.38 (AA', 2H), 7.30–7.13 (m, 5H, Ph), 7.13–7.08 (BB', 2H), 4.14 (s, 2H, CH$_2$), 3.64 (s, 2H, CH$_2$), 1.25 (s, 6H, 2-CH$_3$).

$^{13}$C-NMR ([D$_6$]-DMSO): d (ppm)=194.1 (CO) 170.5 (CO), 132.9, 132.1, 131.7, 131.65, 129.3, 128.6, 127.9, 126.8, 128.4, 127.3, 125.6, 122.9, 54.6 (CH$_2$), 48.9 (C-2), 30.6 (CH$_2$), 24.4 (C(CH$_3$)$_2$).

CHN: calc. C, 70.14; H, 5.12; N, 3.56; fnd C, 70.09; H, 5.09; N, 3.65.

EXAMPLE 19

6-(4-Chlorophenyl)-2,3-dihydro-2,2,5-trimethyl-1-oxo-7-phenyl-1H-pyrrolizine 6-(4-Chlorophenyl)-2,3-dihydro-2,2-dimethyl-1-oxo-7-phenyl-1H-pyrrolizin-5-ylacetic acid (example 18, 0.60 g, 1.52 mmol) is heated at 245° C. for 15 min. The cooled melt is ground and extracted with 10 ml of diethyl ether. The solvent is filtered off with suction and the crystallizate is dried.

Yield: 420 mg (79%). $C_{22}H_{20}ClNO$, 349.9 g/mol, M.p.: 227° C.

IR (K3r): 1/l (cm$^{-1}$)=2966, 2866, 1682 (CO), 1537, 1461, 1399, 1359, 1322, 1125, 1089, 753, 695.

$^1$H-NMR (CDCl$_3$): d (ppm)=7.41–7.36 (AA', 2H), 7.31–7.18 (m, 5H, Ph), 7.11–7.06 (BB', 2H), 4.01 (s, 2H, CH$_2$), 2.25 (s, 3H, CH$_3$), 1.38 (s, 6H, 2-CH$_3$).

$^{13}$C-NMR (CDCl$_3$): d (ppm)=193.8 (CO), 133.4, 132.5, 132.2, 130.9, 131.6, 129.7, 128.6, 127.9, 126.9, 127.2, 125.6, 124.9, 55.0 (C-3), 49.5 (C-2), 25.0 (C(CH$_3$)$_2$), 10.5 (C=C—CH$_3$).

CHN: calc. C, 75.53; H, 5.76; N, 4.00; fnd C, 75.58; H, 5.84; N, 4.13.

EXAMPLE 20 a) Ethyl 2-(6-(4-Chlorophenyl)-2,3-dihydro-2,2-dimethyl-7-phenyl-1H-pyrrolizin-5-yl]-2-hydroxyacetate Ethyl 6-(4-chlorophenyl)-2,3-dihydro-2,2-dimethyl-7-phenyl-1H-pyrrolizin-5-yl]-2-oxoacetate (1.0 g, 2.4 mmol), prepared according to Laufer et al. (J. Med. Chem. 1994, 37, 1894–1897), is dissolved in 10 ml of THF. A solution of 0.03 g of NaBH$_4$ in 3 ml of water is then added and the 2-phase system is stirred at room temperature for 1 h. It is then treated with 3 ml of conc. NH$_3$ solution and stirred again for 1 h. The organic phase is separated off, diluted with about 80 ml of water and extracted twice with 20 ml of diethyl ether. The ether phase is washed three times with 100 ml of water, dried over Na$_2$SO$_4$ and concentrated not entirely to dryness in a rotary evaporator. The product 20a crystallizes after addition of 10 ml of hexane.

Yield: 0.86 g (86%), $C_{25}H_{26}ClNO_3$, 423.9 g/mol, M.p.: 117° C.

IR (KBr): 1/l (cm$^{-1}$)=3456 (OH), 2956, 2870, 1736 (CO ester), 1603, 1448, 1213, 1065, 1014, 698.

$^1$H-NMR ([D$_6$]-DMSO): d (ppm)=7.38–7.34 (AA', 2H), 7.19–7.00 (m, 5H, Ph), 6.99–6.95 (BB', 2H), 5.93 (d, 1H, OH, $^3$J=4.2 Hz), 4.96 (d, 1H, CH, $^3$J=4.4 Hz), 4.20–4.00 (m, 2H. OCH$_2$), 3.84 and 3.67 (2H, AB, 3-H$_2$, $^2$J=11.0 Hz), 2.82 and 2.68 (2H. AB, 1-H$_2$, $^2$J=15.4 Hz), 1.24 (s, 3H, 2-CH$_3$), 1.17 (s, 3H, 2-CH$_3$), 1.16 (t, 3H, OCH$_2$CH$_3$, $^3$J 7.1 Hz).

$^{13}$C-NMR ([D$_6$]-DMSO): d (ppm)=171.6 (CO), 135.5, 134.9, 134.3, 130.7, 131.7, 128.1, 128.0, 127.7, 124.6, 122.8, 122.7, 113.6, 64.8 (CHOH), 60.7 (CH$_2$), 58.8 (CH$_2$), 42.8 (C-2), 39.4 (CH$_2$), 27.4 (CH$_3$), 27.1 (CH$_3$), 14.0 (OCH$_2$CH$_3$).

CHN: calc. C, 70.83; H, 6.18; N, 3.30; fnd C, 71.24; H, 6.38; N, 3.07.

b) 2-[6-(4-Chlorophenyl)-2,3-dihydro-2,2-dimethyl-7-phenyl-1H-pyrrolizin-5-yl]-2-hydroxyacetic Acid Potassium hydroxide (0.50 g) is dissolved in 10 ml of 95% ethanol. Ethyl 6-(4-chlorphenyl)-2,3-dihydro-2,2-dimethyl-7-phenyl-1H-pyrrolizin-5-yl]-2-hydroxyacetate (0.40 g, 0.66 mmol) is added and the mixture is stirred at room temperature for 16 h. The solvent is then removed on a rotary evaporator and the residue is firstly leached with diethyl ether and washed, then treated with 100 ml of water. The solution is acidified to pH 4 using 3 M hydrochloric acid. The white acid which deposits is rapidly taken up in 20 ml of diethyl ether. The organic phase is separated off, washed with 20 ml of water, dried over sodium sulfate, filtered and the solvent is evaporated.

Yield : 0.18 g (68%), $C_{23}H_{22}ClNO_3$, 397.9 g/mol;

IR (KBr): 1/L=3402 (s, br, OH), 2956, 2870 (s, aliphat.+COOH), 1718 (s, CO), 1603, 1099, 1059, 1012, 837, 696.

H-NMR ([D$_6$]-DMSO): d (ppm)=12.8 (s, broad, 1H, COOH), 7.37–6.94 (m, 9H, subst.+unsubst. aromatic), 4.89 (s, 1H, CHOH), 3.83, 3.66 (2H, AB system, CH$_2$, $^2$J=11.0 Hz), 2.80, 2.68 (2H, AB system, CH$_2$, $^2$J, 15.5 Hz), 1.22 (s, 3 H, 2-CH$_3$), 1.17 (s, 3H, 2-CH$_3$). $^{13}$C-NMR ([D$_6$]-DMSO): d=173.3 (COOH), 135.6, 134.7, 134.5, 130.6 (C quart.), 131.7, 128.1, 128.0, 127.7, 124.6 (CH, aromatic), 123.3, 122.7, 113.5 (C quart.), 64.5 (CHOH), 58.8 (CH$_2$), 42.8 (C-2), 39.4 (CH$_2$), 27.4 (CH$_3$), 27.3 (CH$_3$). MS (ES$^+$): m/z=396 (27%; (M+1)$^+$) fragments: m/z=378 (16), 350 (100).

EXAMPLE 21

Ethyl 6-(2-Benzofuranyl)-2,3-dihydro-2,2-dimethyl-1-methoxy-7-phenyl-1H-pyrrolizin-5-yl-2-oxoacetate a) Ethyl 6-(2-Benzofuranyl)-1-bromo-2,3-dihydro-2,2-dimethyl-7-phenyl-1H-pyrrolizin-5-yl-2-oxoacetate Ethyl 6-(2-benzofuranyl)-2,3-dihydro-2,2-dimethyl-7-phenyl-1H-pyrrolizin-5-yl-2-oxoacetate (4.3 g, 10 mmol, Laufer et al. Arch. Pharm. Pharm. Med. Chem. 1997, 330, 307–312.) and NBS (2.0 g, 11 mmol) are refluxed for 2 h with AIBN (100 mg) in CCl$_4$ (100 ml). The succinimide is filtered off from the cooled mixture and the solvent is removed in vacuo and the residue is recrystallized from diethyl ether.

Yield 4.5 g (89%), $C_{27}H_{24}BrNO_4$, 506.41 g/mol;

IR (KBr): 1/l (cm$^{-1}$)=2985, 2966, 1734 (CO ester), 1603, 1457, 1444, 1376, 1267, 1253, 1182, 1169, 1078, 1066, 1014, 760, 725, 693.

$^1$H-NMR ([D$_6$]-DMSO): d (ppm)=7.47–7.20 (m, 9H, 2Ar.), 6.52 (s, 1H, 3-CH furan); 4.97 (s, 1H, CH); 4.38–4.13 (AB , 2H, CH$_2$), 3.75–3.68 (m, 2H, CH$_2$), 1.51 (s, 3H, CH$_3$), 1.28 (s, 3H, CH$_3$); 1.05–0.98 (t, 3H, CH$_3$);

$^{13}$C-NMR ([D$_6$]-DMSO): d (ppm)=177.4, 163.7, 154.7, 148.8, 143.2, 132.5, 129.1, 128.6, 128.5, 128.4; 128.4; 127.4; 124.6; 124.1; 123.8; 123.1; 121.1; 121.1; 111.0; 107.4; 62.2; 59.1; 54.4; 48.3; 26.4; 24.9; 13.5.

b) Ethyl 6-(2-Benzofuranyl)-2,3-dihydro-2,2-dimethyl-1-methoxy-7-phenyl-1H-pyrrolizin-5-yl-2-oxoacetate Ethyl 6-(2-benzofuranyl)-1-bromo-2,3-dihydro-2,2-dimethyl-7-phenyl-1H-pyrrolizin-5-yl-2-oxoacetate (example 21a, 1.52 g, 3 mmol) is suspended in abs. MeOH (40 ml) and stirred at room temperature for 30–45 min until the formation of a fine precipitate. The precipitate is filtered off and washed with MeOH.

Yield: 1.17 g (86.3%), $C_{28}H_{27}NO_5$, 457.53 g/mol,

IR (KBr): 1/l (cm$^{-1}$)=1754 (CO) 1720 , 1641, 1458, 1440, 1431, 1425, 1251, 1187, 1179, 1094, 1088, 1063, 756.

$^1$HNMR ([D$_6$]-DMSO): d (ppm)=7.57–7.23 (m, 9H, 2Ar.); 6.73 (s, 1H, CH); 4.38 (s, 1H, CH); 4.15–4.13 (m, 2H, CH$_2$); 3.60–3.55 (6, 2H, CH$_2$); 3.02 (s, 3H, CH$_3$); 1.24 (s, 3H, CH$_3$); 1.18 (s, 3H, CH$_3$); 0.94–0.87 (t, 3H, CH$_3$).

In Addition to a Little Methyl 6-(2-Benzofuranyl)-2,3-dihydro-2,2-dimethyl-1-methoxy-7-phenyl-1H-pyrrolizin-5-yl-2-oxoacetate $C_{27}H_{25}NO_5$, 443.50 g/mol, $^1$HNMR (CDCl$_3$): d (ppm)=7.55–7.10 (m, 9H, 2Ar.); 6.49 (s, 1H, 3-CH furan); 4.21 (s, 2H, CH$_2$); 4.18 (s, 1H, CH); 3.35 (s, 3H, CH$_3$); 3.06 (s, 3H, CH$_3$); 1.33 (s, 3H, CH$_3$); 1.22 (s, 3H, CH$_3$);

$^1$HNMR ([D6]-DMSO): AB system of the 3-CH$_2$ group.

EXAMPLE 22

6-(2-Benzofuranyl)-2,3-dihydro-2,2-dimethyl-1-methoxy-7-phenyl-1H-pyrrolizin-5-yl-2-oxoacetic Acid Ethyl 6-(2-benzofuranyl)-1-bromo-2,3-dihydro-2,2-dimethyl-7-phenyl-1H-pyrrolizin-5-yl-2-oxoacetate (example 21a, 1.1 g, 2 mmol) are suspended in a methanolic NaOH, prepared from Na (0.52 g, 20 mmol) in MeOH (40 ml), and refluxed for 2 h. After removal of the solvent in vac., the residue is partitioned in water and neutral compounds are extracted with ethyl acetate and discarded. The water phase acidified to pH 3 with HCl (10%) is again extracted with ethyl acetate. The organic phase of the acidic compounds, dried ($Na_2SO_4$) and concentrated.

Yield : 0.65 g (77%), $C_{26}H_{23}NO_5$ , 429.48 g/mol,

IR (KBr): 1/l ($cm^{-1}$)=3430, 2959, 2939, 1721 (CO acid), 1621 (sh), 1608, 1458, 1446, 1369, 1272, 1254, 1081, 1072, 1064, 752.

$^1$HNMR ([D6]DMSO): d (ppm)=7.60–7.15 (m, 9H, 2Ar.); 6.67 (s; H; CH); 4:34 (s, 1H, CH); 4.14–4.11 (AB, 2H, $CH_2$); 3.00 (s, 3H, CH3); 1.24 (s, 3H, CH3); 1.17 (s, 3H, CH3), in $CDCl_3$: no splitting of the methylene group in the 3-position;

$^{13}$CNMR ($CDCl_3$): d (ppm)=179.0; 165.3; 154.0; 148.6; 143.1; 133.1; 128.8; 128.4; 128.3; 127.1; 124.4; 122.9; 122.5; 122.5; 121.4; 121.2; 111.1; 107.2; 82.0; 59.7; 59.7; 57.3; 46.7; 26.1; 20.1.

EXAMPLE 23

6-(2-Benzofuranyl)-2,3-dihydro-2,2-dimethyl-1-methoxy-7-phenyl-1H-pyrrolizin-5-ylacetic Acid Ethyl 6-(2-benzofuranyl)-2,3-dihydro-2,2-dimethyl-1-methoxy-7-phenyl-1H-pyrrolizin-5-yl-2-oxoacetate (example 21b, 0.92 g, 2 mmol) in diethylene glycol (20 ml) is heated at 60° C. for 30 min. with hydrazine hydrate 80% (1.56 ml, 40 mmol), then treated with KOH techn. 85% (2.1 g, 32 mmol) and the mixture is kept at 130° C. for 4 h (until the end of the evolution of gas and fading of the coloration). The mixture, which is poured onto ice, is brought to pH 3 using HCl 10%, and the fine precipitate is filtered off with suction and dried over $P_2O_5$.

For purification, the crude acid (1.0 g) is adsorbed on neutral $Al_2O_3$, impurities are removed by elution with diethyl ether, then desorbed using a sat. $NaH_2PO_4$ solution and taken up in ether. The filtered ether extract is concentrated to dryness.

Yield: 0.45 g, $C_{26}H_{25}NO_4$, 415.49 g/mol.

$^1$HNMR ([D6]DMSO): d (ppm)=12.6 (b, 1H, COOH), 7.60–7.15 (m, 9H, 2Ar.); 6.46 (s, 1H; 3-CH furan), 4.23 (s, 1H, 1-CH); 3.90–3.65 (2AB, 4H, $2CH_2$), 2.95 (s, 3H, $OCH_3$); 1.24 (s, 3H, CH3); 1.13 (s, 3H, $CH_3$).

$^{13}$CNMR ($CDCl_3$): d (ppm)=11.3; 163.6; 162.6; 145.4; 143.7; 138.7; 138.5; 138.1; 135.9; 133.2; 132.55; 132.43; 130.3; 128.3; 122.3; 120.5; 112.3; 92.6; 66.2; 65.7; 57.1; 41.2; 36.6; 30.45.

EXAMPLE 24

2-[6-(2-Benzofuranyl)-2,3-dihydro-2, 2-dimethyl-1-methoxy-7-phenyl-1H-pyrrolizin-5-yl]-2-hydroxyacetic Acid From ethyl 2-[(6-(2-benzofuranyl)-2,3-dihydro-2,2-dimethyl-7-phenyl-1H-pyrrolizin-5-yl]-2-oxoacetate (S. Laufer, et al. Arch. Pharm. Pharm Med. Chem. 1997, 330, 307–312) according to the method described in example 20.

Yield: 0.28 g (65%) crystallized from diethyl ether, $C_{27}H_{27}NO_4$, 429.52.

IR (KBr): 1/l ($cm^{-1}$)=3431, 2958, 1730 (CO ester), 1603, 1454, 1369, 1254, 1164, 1065, 1024, 751, 700.

$^1$HNMR ($CDCl_3$): d (ppm)=7.55–7.10 (m, 9H, 2Ar.) 6.50 (d; 1H; 3-CH furan, J=0.6 Hz), 5.53 (d, 1H, C$\underline{H}$OH, J=2.0 Hz), 4.35–4.1 ($ABX_3$, 2H, O—C$\underline{H}_2CH_3$); 3.68/3.62 (AB, 2H, $J_{AB}$=10.6 Hz, $CH_2$), 3.39 (d, OH, J=2.0 Hz), 2.80/2.67 (AB, 2H, CH2, $J_{AB}$=15 Hz); 1.35–1. 15 (2s+t, 9H, $C(CH_3)_2$, $OCCH_2C\underline{H}_3$).

$^{13}$CNMR ($CDCl_3$): d (ppm)=172.9; 154.4; 152.1, 135.9, 135.4, 129.2, 128.2, 128.1, 125.4, 123.3, 122.4, 120.3, 115.7, 114.7, 111.0, 104.1, 65.7, 62.5, 58.9, 53.5, 39.8, 27.9, 27.6, 14.1.

EXAMPLE 25

2-[2-(4-Chlorophenyl)-6-hydroxymethyl-6-methyl-1-phenyl-6,7-dihydro-5H-pyrrolizin-3-yl]acetic Acid a) 5-Hydroxymethyl-2,2,5-trimethyl-1,3-dioxane 2,2-Bishydroxymethyl-1-propanol (12.0 g, 0.1 mol) is suspended in toluene abs. (50 ml). The suspension, adjusted to a temperature of 75° C., is treated with 2,2-dimethoxypropane (10.9 g, 13 ml, 0.105 mol) and toluenesulfonic acid monohydrate (0.95 g, 5 mmol). The mixture is kept at 80–85° C. for 5 h with intensive stirring. The liberated methanol is distilled off over an attached bridge, then the mixture is cooled.

Using semisaturated $Na_2CO_3$ solution, the toluene phase is extracted with shaking and deposited sodium tosylate is brought into solution again using water (20 ml). The phases are separated, and the water phase is back-extracted 2 times with toluene (50 ml) and then discarded. The collected toluene solutions are washed with saturated NaCl solution (50 ml) and dried over $Na_2SO_4$ sicc. The solvent is removed under reduced pressure after filtration of the drying agent. 12.5 g of crude product, of 95% purity (according to gc determination), are obtained as an oily residue.

Yield: 75%=12.5 g (95%), $C_8H_{16}O_3$, MW=160.21; C, 59.98%; H, 10.07%; O, 29.96%;

IR (NaCl): 1/λ ($cm^{-1}$) 3456, 2992, 2953, 2871, 1454, 1372, 1266, 1207, 1086, 1050, 1039, 830;

1HNMR ($CDCl_3$): δ (ppm)=3.65 (9; 6H, $3CH_2$), 2.64 (s, 1H, OH), 1.44 (s; 3H, $CH_3$), 1.40 (s, 3H, $CH_3$), 0.83 (s; 3H, $CH_3$), $^{13}$CNMR ($CDCl_3$): δ (ppm)=125.3, 97.0, 65.4, 63.7, 34.3, 25.9, 21.6, 21.0, 17.7.

b) 5-Benzyloxy-2,2,5-trimethyl-1,3-dioxane

5-Hydroxymethyl-2,2,5-trimethyl-1,3-dioxane (12.0 g, 75 mmol), dissolved in toluene abs. (120 ml), is treated with a suspension of NaH (60%, 4.8 g, 120 mmol) in toluene (20 ml), which has been washed 2 times beforehand with hexane (10 ml each). As soon as the evolution of hydrogen comes to a halt, the mixture is heated at 100° C. for 20 min., then a solution of benzyl chloride (10.13 g, 80 mmol) in toluene (20 ml) is added dropwise to the still hot reaction solution and the mixture is refluxed for a number of hours until reaction is complete (5–10 h).

It is then treated with $NaHCO_3$ solution (120 ml) and the mixture of phases is stirred. The water phase separated off in the separating funnel is extracted 2 times with toluene (160 ml), and the combined toluene phases are washed with sat. NaCl solution and dried over $Na_2CO_3$ sicc. The organic phase filtered from the drying agent is concentrated in vacuo. 18.6 g of a yellowish oil remain (contaminated with 3.7% of benzyl chloride).

Yield: 99.6%=18.6 g (96.3%), $C_{15}H_{22}O_3$, MW=250.34; C, 71.97%; H, 8.86%; O, 19.17%;

IR (NaCl): 1/λ ($cm^{-1}$)=2990, 2860, 1453, 1370, 1208, 1089, 1028, 831, 733, 698;

$^1$HNMR ($CDCl_3$): δ (ppm)=7.34–7.18 (m, 5H, arom.), 4.54 (s, 2H), 3.77–3.71/3.58–3.52 (AB, 4H), 3.4.7 (s, 2H), 1.42 (s, 3H), 1.38 (s, 3H), 0.90 (s, 6H).

¹³CNMR (CDCl₃): δ (ppm)=138.7, 129.0, 128.8, 127.3, 125.3, 97.8, 73.3, 73.1, 66.6, 34.4, 26.3, 21.4, 21.1, 18.3.

c) 2-Benzyloxymethyl-2-methy-1,3-propanediol

The solution of 5-benzyloxymethyl-2,2,5-trimethyl-1,3-dioxane (12.5 g, 50 mmol) in MeOH (250 ml) is treated at room temperature with trifluoroacetic acid (90%, 10 ml). After 1 h, a gc sample is checked for completeness of the cleavage; if necessary the reaction is completed by addition of trifluoroacetic acid (90%) and stirring for 1 hour. The mixture is neutralized by addition of a saturated $Na_2CO_3$ solution (25 ml) and concentrated in vacuo to a quarter of the original volume. After addition of water until the dissolution of deposited salts (100 ml), the mixture is extracted 4 times in a separating funnel using ethyl acetate (400 ml). The combined ethyl acetate phases are dried over $Na_2SO_4$ sicc. and concentrated in vacuo after filtering. 9.82 g of a pale yellow, viscous oil of about 90% purity (gc) are obtained.

Yield: 93.5%=9.82 g (90%), MW=210.28; $C_{12}H_{18}O_3$; C, 68.55%; H, 8.63%; O, 22.83%;

IR (NaCl): 1/λ (cm⁻¹) 3385, 2875, 1454, 1364, 1098, 1045, 737, 698;

¹HNMR (CDCl₃): δ (ppm)=7.35–7.28 (5H, arom.) 4.51 (s; $CH_2$), 3.73–3.54 (AB, 4H, $2CH_2$), 3.46 (s; $CH_2$), 2.73 (s; OH), 0.82 (s; $CH_3$);

¹³CNMR (CDCl₃): δ (ppm)=137.9, 128.5, 127.8, 127.5, 75.6, 73.6, 67.8, 40.8, 17.1.

d) 5-Benzyloxymethyl-5-methyl-1,3-dioxa-2-thiane 2-oxide

2-Benzyloxymethyl-2-methyl-1,3-propanediol (84.07 g, 0.4 mol) is dissolved in $CH_2Cl_2$ (420 ml). Thionyl chloride (61.88 g, 38 ml, 0.52 mol), dissolved in $CH_2Cl_2$ (100 ml), is added dropwise with cooling of the batch in an ice water bath such that the evolution of HCl can be kept under control (20 min.). The mixture is then stirred at room temperature for a further hour, the evolution of HCl coming to a halt.

The entire batch is poured onto ice water and neutralized using a saturated $Na_2CO_3$ solution (200 ml). The alkaline water phase is rapidly extracted with $CH_2Cl_2$ (300 ml) a further 3 times and the combined $CH_2Cl_2$ phases are washed with saturated sodium chloride solution, dried over $Na_2SO_4$ sicc., filtered and finally concentrated. 97.17 g of an easily mobile, yellow oil of 95.3% purity remain as a residue.

Yield: 94.8%=97.17 g (95.3%), $C_{12}H_{16}O_4S$, MW=256.32; C, 56.23%; H, 6.29%; O, 24.97%; S, 12.51%;

IR (NaCl): 1/λ (cm⁻¹)=¹HNMR (CDCl₃): δ (ppm)= 7.37–7.24 (m; 5H, arom.), 4.60–4.54/3.73–3.67 (AB, $2CH_2$), 4.58 (s; $CH_2$), 3.63 (s; $CH_2$), 0.87 (s; $CH_3$); isomer: 7.37–7.24 (m; 5H, arom.), 4.89–4.83/3.52–3.47 (AB, $CH_2$), 4.46 (s; $CH_2$), 3.16 (s; $CH_2$), 1.29 (s; $CH_3$);

¹³CNMR (CDCl₃): δ (ppm)=138.1, 128.3, 127.6, 127.4, 73.6, 73.3, 62.0, 35.7, 18.2; Isomer: 137.6, 128.4, 127.8, 127.6, 72.0, 71.1, 64.1, 36.0, 18.4.

e) 4-Benzyloxy-3-hydroxymethyl-3-methylbutyronitrile

NaCN (25.48 g, 0.52 mol) is added to the solution of 5-benzyloxy-methyl-5-methyl-1,3-dioxa-2-thiane 2-oxide (102.53 g, 0.4 mol) in DMSO abs. (480 ml) and it is then heated to an internal temperature of 105° C. The rapidly darkly discoloring mixture is stirred overnight (16–20 h) at this temperature and a sample is checked by means of gc for the extent of the reaction. 2 thirds of the DMSO employed (320 ml) are distilled off from the reaction mixture in vacuo and, after cooling, the residue which remains is poured onto water (1.5 l). The alkaline mixture is rendered weakly acidic (pH 4) using dil. HCl (3%) and extracted 4 times with diethyl ether (1.2 l). The collected ether phases are combined, washed with sat. NaCl solution (200 ml) and dried over $Na_2SO_4$ sicc. After concentrating the filtered ether phase in vacuo, 91.16 g of red-brown oil of 90% purity (gc) remain.

Yield: 95.9%=91.16 g (90%), $C_{13}H_{17}NO_2$, MW=219.29; C, 71.21%; H, 7.81%; N, 6.39%; O, 14.59%

IR (NaCl): 1/λ (cm⁻¹) 3483, 2961, 2925, 2863, 2245, 1454, 1100, 740, 699;

¹HNMR (CDCl₃): δ (ppm)=7.38–7.26 (m; 5H, arom.), 4.53 (s; $CH_2$—Ph), 3.66–3.61/3.45–3.44 (AB; $CH_2$—OH), 3.44 (s; $CH_2$—O—), 2.67–2.59/2.50–2.42 (As; $CH_2$—CN), 1.01 (s; CH3);

¹³CNMR (CDCl₃): δ (ppm)=137.4, 128.5, 128.0, 127.6, 118.1, 75.5, 73.7, 68.6, 38.8, 23.0, 19.1.

f) 4-Benzyloxy-3-chloromethyl-3-methylbutyronitrile

4-Benzyloxy-3-hydroxymethyl-3-methylbutyronitrile (7.13 g, 32 mmol) and pyridine (2.45 g, 2.5 ml, 31 mmol) are dissolved in dichloroethane abs. (15 ml) under argon. A solution of thionyl chloride (4.64 g, 2.8 ml, 39 mmol) in dichloroethane abs. (6 ml) is slowly added dropwise starting at room temperature. The mixture heats to 60° C. in the course of this, and the reaction mixture is kept at this temperature overnight (16–20 h) by heating. The mixture is then poured onto water (200 ml), to which saturated $Na_2CO_3$ solution (35 ml) has been admixed for neutralization.

The mixture is extracted with 3 portions of ether (300 ml), and the ether solution obtained is washed with sat. NaCl solution (100 ml), dried over $Na_2SO_4$ sicc. and concentrated. The black crude material obtained as a residue (7.51 g, 91%) of 72% purity (gc) is fractionally distilled.

At 200° C./2 10⁻³ mbar, 6.57 g (85.5%) of pale yellow oil distill over (75% according to gc).

Yield: 85.5%=6.57 g (75%), $C_{13}H_{16}ClNO$, MW=237.73; C, 65.68%; H, 6.78%; Cl, 14.91%; N, 5.89%; O, 6.73%

IR (NaCl): 1/λ (cm⁻¹)=2863, 2245, 1737, 1454, 1207, 1101, 740, 699;

¹NMR (CDCl₃): δ (ppm) 7.35–7.24 (m; 5H, arom.), 4.53 (s; $CH_2$—Ph), 3.65–3.50 (AB; $CH_2$—Cl), 3.39 ($CH_2$—O), 2.51 ($CH_2$—CN), 1.17 ($CH_3$);

¹³CNMR (CDCl₃): δ (ppm) 137.6, 128.4, 127.8, 127.5, 73.5, 73.1, 49.8, 39.4, 24.0, 20.0.

g) 5-Benzyl-3-(benzyloxymethyl)-3-methyl-3,4-dihydro-2H-pyrrole

A benzylmagnesium chloride solution in ether (224 ml, 1 M, 0.224 mol) is heated to 30° C. and a solution of 4-benzyloxy-3-chloromethyl-3-methylbutyronitrile (75%, 40 g, 0.126 mol) in diethyl ether (140 ml) is slowly added dropwise (30 min.). The suspension formed is kept at reflux by warming after complete addition. After 2 h, the ether (310 ml) is distilled off (45 min.) and then replaced by toluene abs. (210 ml). The yellow toluene suspension is heated to 100° C. and then stirred at this temperature for 2 h. The batch, which is cooled to room temperature, is treated with dil. HCl (10% strength, 100 ml) and stirred until, in addition to the aqueous and the toluene phase, a third, oily phase separates. The oil phase and water phase are separated off, and the toluene phase is extracted 2 times in a separating funnel with dil. HCl (100 ml). The oil phase combined with the HCl phases is washed with toluene (50 ml) and then adjusted to pH 8–9 with NaOH (32%). After stirring for 30 min., the separated oily base fraction is taken up with diethyl ether, and the alkaline water phase is extracted a further 3 times with ether (450 ml). The collected ether extracts are dried over $Na_2SO_4$ sicc. and concentrated. A red-brown oily residue of 39.64 g (96% of theory, 78% according to gc) remains.

Yield: 96%=39.64 g (78%), MW=293.41; $C_{20}H_{23}NO$; C, 81.87%; H, 7.90%; N, 4.77%; O, 5.45%;

¹HNMR (CDCl₃): δ (ppm)=7.37–7.17 (m; arom.), 4.45 (s; $CH_2$) 3.74–3.63/3.47–3.4 (AB; $CH_2$), 3.63 (s; $CH_2$), 3.19 (s; $CH_2$), 2.53–2.45/2.17–2.09 (AB, $CH_2$), 1.04 (a; $CH_3$).

$^{13}$CNMR (CDCl$_3$): δ (ppm) 176.7, 141.6, 138.7, 136.9, 135.7, 133.6, 130.7, 129.7, 129.2, 128.9, 128.8, 128.7, 128.6, 128.5, 127.9, 127.8, 127.7, 127.6, 127.1, 127.0, 126.9, 77.0, 73.6, 73.4, 72.7, 70.4, 65.1, 47.5, 46.6, 43.0, 42.2, 41.1, 24.0.

h) 2-(Benzyloxymethyl)-6-(4-chlorophenyl)-2-methyl-7-phenyl-2,3-dihydro-1H-pyrrolizine 5-Benzyl-3-(benzyloxymethyl)-3-methyl-3,4-dihydro-2H-pyrrole (108 g, 0.368 mol), 2-bromo-1-(4-chlorophenyl)-1-ethanone (100 g, 0.428 mol) and NaHCO$_3$ (34.6 g, 0.42 mol) are dissolved in methanol abs. (950 ml) in a 2 l flask and, adjusted to a temperature of 40° C., stirred for a total of 2 d with exclusion of light. The supernatant methanol phase is poured off from the viscous, green-brown substance at the bottom of the solution formed during the reaction, and the material is taken up with diethyl ether (1 l) and water (800 ml) and partitioned. The water phase is extracted 2 times with ether (600 ml). The collected ether solution is dried over Na$_2$SO$_4$ sicc. and concentrated. Solvent residues are removed in a high vacuum. 124 g of a viscous, swelling residue remain, which consists of the compound sought and which can be employed for. further reactions without further purification. For characterization, the substance is purified by means of column chromatography (Al$_2$O$_3$/hexane-diethyl ether 4:1).

Yield: 78.8%=124 g, C$_{26}$H$_{26}$ClNO, MW=427.98; C, 78.58%; H, 6.12%; Cl, 8.28%; N, 3.27%; O, 3.74%;

$^1$HNMR (CDCl$_3$): δ (ppm)=7.35–7.12 (m; arom.) 6.67 (B; 1H), 4.54 (s; CH$_2$), 4.09–4.04/3.7–3.66 (AB; CH$_2$), 3.42 (s; CH$_2$), 3.01–2.93/2.75–2.67 (AB; CH$_2$), 1.33 (s; CH$_3$);

$^{13}$CNMR (CDCl$_3$): δ (ppm)=138.2, 136.0, 135.1, 135.0, 131.0, 129.8, 129.4, 129.3, 129.1, 128.7, 128.5, 128.3, 128.2, 128.1, 127.6, 127.5, 127.4, 127.3, 125.6, 125.0, 114.2, 113.2, 76.3, 73.2, 55.6, 47.6, 30.8, 24.0.

i) Ethyl 6-(Benzyloxymethyl)-2-(4-chlorophenyl-)-6-methyl-1-phenyl-6,7-dihydro-5H-pyrrolizin-3-yl-2-oxoacetate The solution of ethyl oxalyl chloride in THF (50 ml) is added drop-wise at room temperature to the solution of 2-(benzyloxy-methyl)-6-(4-chlorophenyl)-2-methyl-7-phenyl-2,3-dihydro-11-pyrrolizine (19.02 g, 44.4 mmol) in THF abs. (240 ml) and the mixture is stirred for a further 45 min., after which a tlc sample (SiO$_2$/diisopropyl ether-hexane 1:1) no longer indicates starting material.

The pink- to lilac-colored solution is treated with water (240 ml) and neutralized with Na$_2$CO$_3$ soln (10% strength, 80 ml). The oil phase separating from the yellow-colored mixture is separated off in a separating funnel. The THF-containing water phase is extracted 2 times with diethyl ether (200 ml) and the ether phases are combined with the oil phase. The ether solution is washed with saturated NaCl solution (100 ml), dried over Na$_2$SO$_4$ sicc. and concentrated. 21.57 g (91.9% of theory) of a yellow oil remain as a residue.

Yield: 91.9%=21.57 g, C$_{32}$H$_{30}$ClNO$_4$, MW=528.05. C, 72.79%; H, 5.73%; Cl, 6.71%; N, 2.65%; O, 12.12%;

IR (NaCl): 1/λ (cm$^{-1}$)=1746; 1637; 1450; 1427; 1250; 1093; 1063; 1014; 768; 700;

$^1$HNMR (CDCl$_3$): δ (ppm)=7.34–6.93 (m, 14H, arom.), 4.55 (s, 2H, CH$_2$), 4.51–4.16 (AB, CH$_2$), 3.62–3.55 (q, 2H, CH$_2$), 3.44 (s, 2H, CH$_2$), 3.18–2.67 (AB, CH$_2$), 1.33 (s, 3H, CH$_2$), 1.09–1.02 (t, 3H, CH$_3$);

j) Ethyl 6-(Benzyloxymethyl)-2-(4-chlorophenyl-)-6-methyl-1-phenyl-6,7-dihydro-5H-pyrrolizin-3-ylacetate Ethyl 6-(benzyloxymethyl)-2-(4-chlorophenyl-)-6-methyl-1-phenyl-6,7-dihydro-5H-pyrrolizin-3-yl-2-oxoacetate (19.54 g, 37 mmol), sodium cyanoborohydride (17.43, 277 mmol) and zinc(II) iodide (16.81 g, 52 mmol) are introduced successively into abs. CH$_2$Cl$_2$ (300 ml) and the mixture is stirred at room temperature. After 2 h, a TLC check (SiO$_2$/diisopropyl ether-hexane 1:1) no longer shows any starting material.

After this, water (300 ml) is added and the mixture is adjusted to pH 4 using dil. phosphoric acid (8%). The water phase which is separated off is extracted a further 2 times with CH$_2$Cl$_2$ (200 ml), and the combined CH$_2$Cl$_2$ extracts are washed with saturated NaCl solution (100 ml). After drying over Na$_2$SO$_4$ sicc. and concentrating, 19.10 g of a red-brown resin (100% of theory) remain.

Yield: 100%=19.10 g, C$_{32}$H$_{32}$ClNO$_3$, MW=514.07; C, 74.77%; H, 6.27%; Cl, 6.90%; N, 2.72%; O, 9.34%;

$^1$HNMR (CDCl$_3$): δ (ppm)=7.34–7.02 (m, 14H, 3 aromat.), 4.55 (s, 2H, CH$_2$), 4.25–4.10 (q, 2H, CH$_2$), 4.07–3.68 (AB, CH$_2$), 3.50 (s, 2H; CH$_2$), 3.50–3.40 (AB, CH$_2$), 3.05–2.72 (AB, CH$_2$); 1.35 (s, 3H, CH$_3$), 1.30–1.12 (t, 3H, CH$_3$);

$^{13}$CNMR (CDCl$_3$): δ (ppm)=170.7; 138.3; 135.9; 134.6; 133.4; 131.6, 128.4; 128.2; 128.2; 128.0; 127.6; 127.5; 124.6; 123.8; 117.6; 114.6; 73.3; 61.1; 54.3; 47.5; 36.1; 31.5; 24.1; 14.2.

k) Ethyl 2-(4-Chlorophenyl-)-6-hydroxymethyl-6-methyl-1-phenyl-6,7-dihydro-5H-pyrrolizin-3-ylacetate The solution of ethyl 6-(benzyloxymethyl)-2-(4-chlorophenyl-)-6-methyl-1-phenyl-6,7-dihydro-5H-pyrrolizin-3-ylacetate (49.23 g, 96 mmol) in abs. CH$_2$Cl$_2$ (500 ml) is cooled to −35° C. and treated dropwise with a solution of boron tribromide (96 g, 383 mmol) in abs. CH$_2$Cl$_2$ (250 ml), the solution turning deep red. The mixture is stirred at this temperature for half an hour after complete addition (1 h) and then cautiously neutralized to pH 4 using Na$_2$CO$_3$ solution (10%, 400 ml). The CH$_2$Cl$_2$ phase is separated off in the separating funnel, washed with water and dried over Na$_2$SO$_4$ sicc. After evaporation of the solvent, 46.8 g (115%) remain, which are taken up in diethyl ether and filtered through an Al$_2$O$_3$-packed column (neutral, activity II, 500 g). The column is rinsed 4 times with a mixture of ethyl acetate and ether (1:1, 400 ml). After concentrating the filtrates collected, 37.12 g of a red-yellow oil are obtained as a residue (91.2%).

Yield: 91.2%=37.12 g, C$_{25}$H$_{26}$ClNO$_3$, MW=423.94; C, 70.83%; H, 6.18%; Cl, 8.36%; N, 3.30%; O, 11.32%;

IR (KBr): 1/λ (cm$^{-1}$)=3464; 2925; 1732; 1602; 1529; 1487; 1450; 1176; 1096; 1029; 1013; 831; 765; 700;

$^1$HNMR ([d$_4$]-MeOH): δ (ppm), 7.26–6.99 (m, 9H, aromat.), 4.20–4.05 (q, 2H, CH$_2$), 4.00–3.65 (AB, CH$_2$), 3.52 and 3.54 (2 s, 4H, 2CH$_2$), 3.02–2.63 (AB, CH$_2$), 1.29 (s, 3H, CH$_3$), 1.29–1.17 (t, 3H, CH$_3$);

$^{13}$CNMR ([d$_4$]-MeOH) δ (ppm)=172.7; 137.5; 136.6; 134.6; 132.8; 132.6; 129.3; 129.2; 129.0; 125.7; 124.7; 119.1; 116.0; 69.0; 62.2; 54.8; 36.3; 32.1; 23.5; 14.5;

l) 2-(4-Chlorophenyl-)-6-hydroxymethyl-6-methyl-1-phenyl-6,7-dihydro-5H-pyrrolizin-3-ylacetic Acid The ethyl 2-(4-chlorophenyl-)-6-hydroxymethyl-6-methyl-1-phenyl-6,7-dihydro-5H-pyrrolizin-3-ylacetate (74.0 g, 175 mmol) dissolved in ethanol (160 ml) is treated at room temperature with dil. NaOH (10% strength, 290 ml). After the mixture has been stirred at room temperature for 45 min., it is neutralized (pH 9) with dil. H$_3$PO$_4$ (8%, 150 ml). The separated Na salt is collected by means of filtration, sucked dry and adhering ester is washed off with diisopropyl ether (200 ml). The purified salt is resuspended in water (300 ml) and precipitated as the acid at pH 2–3 using dil. H$_3$PO$_4$ (8%, 380 ml). The precipitated acid is washed with water until the wash liquid gives a neutral reaction and finally dried in vacuo over $P_2O_5$ (14.6 g, 19.8%). The sodium salt mother liquor and filtrates are collected, brought to pH 2–3 using dil. $H_3PO_4$ (8%, 380 ml) and the deposited acid is taken up in ether (400 ml). After washing with sat. NaCl solution (100 ml) and drying over $Na_2SO_4$ sicc., the solvent is evaporated in vacuo. The residue which remains (45.01 g, 53%) is crystallized from diisopropyl ether (250 ml). 21.36 g having a purity of 71.9% crystallize.

The two solids obtained are treated with ultrasound in the presence of heat together with a $CH_2Cl_2$-THF-ethyl acetate mixture (1:1:3, 200 ml) and, after filtering off with suction, (23.2 g, 92%) are recrystallized from acetone (0.7 l). 19 g of acid (25%) having a purity of 96.8% are finally obtained.

Yield: 25%, 19 g, $C_{23}H_{22}ClNO_3$, MW=395.89; C, 69.78%; H, 5.60%; Cl, 8.96%; N, 3.54%; O, 12.12%;

IR (KBr): $1/\lambda$ $(cm^{-1})$=3269; 2958; 1683; 1603; 1531; 1485; 1396; 1305; 1290; 1103; 1034; 1014; 831; 762; 694;

$^1$HNMR ($[d_6]$-DMSO): $\delta$ (ppm)=7.31–7.03 (m, 9H, aromat.), 6.01 (2OH, br.), 4.06–3.67 (AB, $CH_2$), 3.54 (s, 2H, $CH_2$), 3.50 (s, 2H, $CH_2$), 3.07–2.68 (AB, $CH_2$), 1.31 (s, 3H, $CH_3$);

$^{13}$CNMR ($[d_6]$-DMSO): $\delta$ (ppm)=171.8; 135.9; 135.0; 133.2; 131.3 (CH); 130.3; 128.2 (CH); 128.1 (CH); 127.6 (CH); 124.4 (CH); 122.0; 118.6; 113.3; 67.1 ($CH_2$); 53.5 ($CH_2$); 48.0 (Cq); 35.0 ($CH_2$); 31.0 ($CH_2$); 23.5 ($CH_3$).

EXAMPLE 26

2-(4-Chlorophenyl)-6,6-dimethyl-1-phenyl-6,7-dihydro-5H-pyrrolizin-3-yl Benzoate A solution of 6-(4-chlorophenyl)-2,2-dimethyl-7-phenyl-2,3-dihydro-1H-pyrrolizine (1.6 g, 5 mmol, prepared according to Laufer et al. J. Med. Chem. 1994, 37, 1894–7), in anhydrous diethyl ether (100 ml) is cooled to $-70°$ C. under argon and a solution of tert-butyllithium (3.13 ml, 1 molar/15% strength, 5 mmol) in n-pentane is added dropwise with stirring at this temperature such that the initially occurring red coloration of the solution changes to yellow again. After stirring at $-70°$ C. for a further 2 h, the batch solution is allowed to warm to room temperature and the stirring is continued for a further 1 h to complete the anion formation, until it is cooled to $-70°$ C. again. A solution of dibenzoyl peroxide (1.93 g, 75–80% strength, moistened with $H_2O$, 6 mmol) in diethyl ether (50 ml) dehydrated using $CaCl_2$ and molecular sieve 3 Å is added dropwise to the solution of the 3-lithiated 2-(4-chlorophenyl)-6,6-dimethyl-1-phenyl-6,7-dihydro-5H-pyrrolizine thus prepared. The mixture is allowed to warm to room temperature and stirred until the complete disappearance of the starting compound (16–20 h). The solution is treated with water and the water phase is extracted 2 times (100 ml) with diethyl ether. The ether phase is dried over $Na_2SO_4$ sicc. and the solvent is completely removed under reduced pressure after filtration of the drying agent. The residue is recrystallized from n-hexane in the presence of heat. 1.16 g (53% of theory) of melting point 193° C. are obtained as a crystallizate.

Yield: 53%=1.16 g, $C_{28}H_{24}ClNO_2$, MW=441.96; calc.: C, 76.10%; H, 5.47%; Cl, 8.02%; N, 3.17%; O, 7.24%;

IR (NaCl): $1/\lambda$ $(cm^{-1})$ 2956; 1745; 1601; 1542; 1450; 1258; 1176; 1054; 1014; 831; 768; 699;

$^1$HNMR ($CDCl_3$): $\delta$ (ppm)=8.15–8.11 (m, 2H, arom.); 7.70–7.40 (m, 3H, arom.); 7.25–7.10 (m, 9H, aromatic); 3.66 (s, 2H, $CH_2$); 2.86 (s, 2H, $CH_2$); 1.29 (s, 6H, $C(CH_3)_2$);

$^{13}$CNMR ($CDCl_3$): $\delta$ (ppm)=165.0; 135.8; 134.1; 132.7; 131.2; 130.5; 130.4; 129.6; 129.1; 128.7; 128.4; 128.2; 128.1; 125.0; 113.4; 110.8; 77.2; 59.1; 43.5; 40.3; 27.8;

MS ($ES^+$, 35 V), m/z=442/444 (($M+H)^+$, 100%).

EXAMPLE 27

2-(4-Chlorophenyl)-6,6-dimethyl-1-phenyl-6,7-dihydro-5H-pyrrolizin-3-yl[2-(4-chlorophenyl)-6,6-dimethyl-1-phenyl-6,7-dihydro-5H-pyrrolizin-3-yl] acetate A solution of 2-(4-chlorophenyl)-6,6-dimethyl-1-phenyl-6,7-dihydro-5H-pyrrolizin-3-yl)acetic acid (38.0 g; 0.1 mol) in anhydrous diethyl ether (400 ml) is treated at room temperature with $BF_3$ etherate (2 ml, 2.26 g, 0.016 mol) and stirred for 30 min. The solution, which is discolored violet in this time, is then concentrated under reduced pressure (200 ml) and made up with n-heptane (200 ml). Further ether (150 ml) is distilled off under reduced pressure and the crystallizing, violet-colored residue is separated from the ether-heptane mother liquor. The mother liquor is concentrated to dryness (5.5 g) and taken up in ethanol (50 ml) in the presence of heat. After refrigeration (16 h), the blue solution is filtered off with suction from the insoluble residue. The crystallizate is washed with ice-cold ethanol, and, if required, recrystallized again from a little ethanol (10 ml). 0.45 g of the compound sought is obtained. The substance can also be purified by column chromatography ($SiO_2$ hexane ether 9:1) (rf 0.2, ethyl ester rf 0.22).

Yield: 1.3%=0.45 g, $C_{44}H_{40}Cl_2N_2O_2$, MW=699.73; calc.: C, 75.53%; H, 5.76%; Cl, 10.13%; N, 4.00%; O, 4.57%; fnd: C, 75.14%; H, 5.75%; N, 4.07%;

IR (NaCl): $1/\lambda$ $(cm^{-1})$=2960; 2872; 1768; 1601; 1541; 1536; 1451; 1112; 1094; 1012; 833; 698;

$^1$HNMR ($CDCl_3$): $\delta$ (ppm)=7.25–7.01 (m, 18, arom.); 3.71 (s, 2H, $CH_2$) 3.52 (s, 2H, $CH_2$); 3.41 (s, 2H, $CH_2$); 2.81 (s, 2H, $CH_2$); 2.78 (s, 2H, $CH_2$); 1.27 (s, 6H, $C(CH_2)_2$); 1.15 (s, 6H, $C(CH_3)_2$);

$^{13}$CNMR ($CDCl_3$): $\delta$ (ppm)=27.80; 31.06; 40.17; 40.37; 43.06; 43.51; 57.81; 58.21; 110.66; 113.33; 115.06; 115.91; 124.14; 124.77; 125.07; 128.09; 128.12; 128.13; 128.24; 128.35; 128.44; 129.04; 129.36; 130.41; 131.19; 131.56; 131.84; 132.47; 134.58; 134.66; 135.50; 135.74; 169.13;

MS (70 eV, PI-FDMS, +VE, +HMR, B scan), m/z=698.2 ($M^+$, 100%) 699.2 ($M^+$, 50%), 700.2 ($M^+$, 75%), 701.2 ($M^+$, 35%), 702.3 ($M^+$, 18%).

MS ($ES^+$, 35 V), m/z (% rel. intens.) $(M+H)^+$: 699 (32), 700 (18), 701 (20), 702 (10), 703 (7); 334 (65), 335 (15), 336 (100), 337 (25), 338 (80), 339 (18), 340 (19).

MS (EI, 70 eV), m/z (% rel. intens.) ($M^+$: 698+(1), 699 (0.7), 700 (1), 334 (100), 335 (42), 336 (60), 337 (58), 338 (18), 339 (15).

EXAMPLE 28

2-(4-Chlorophenyl)-7a-hydroxy-6,6-dimethyl-1-phenyl-5,6,7,7a-tetrahydropyrrolizin-3-one The [2-(4-chlorophenyl)-6,6-dimethyl-1-phenyl-6,7-dihydro-5H-pyrrolizin-3-yl]benzoate (0.4 g, 0.9 mmol) described in example 26 is suspended in MeOH (20 ml) and treated with NaOH solution (1 ml, 10% strength) and then refluxed for 3 h until the disappearance of the starting material (tlc: $SiO_2$/diisopropyl ether, rf 0.95), then the alcohol is removed in vacuo. The aqueous residue is treated with water (20 ml) and diethyl ether (30 ml) and rendered acidic (pH 2–3) with HCl (10% strength). The ether phase is separated off, the water phase is extracted three times with ether (100 ml) and the collected ether phases are combined, dried over Na$_2$SO$_4$ sicc. and the solvent is concentrated under reduced pressure. 0.39 g of solid of a substance mixture which is purified by column chromatography (SiO$_2$/diisopropyl ether, rf 0.55) remains as a residue. Fractions 8–13 (10 ml each) contain 120 mg (40%) of the title compound.

Yield: 40%=120 mg, C$_{21}$H$_{20}$ClNO$_2$, MW=353.85;

calc.: C, 71.28%; H, 5.70%; Cl, 10.02%; N, 3.96%; O, 9.04%;

IR (NaCl): 1/λ (cm$^{-1}$) 3355; 1680; 1394; 1092; 1068; 696; 530;

$^1$HNMR (DMSO-d$_6$): δ (ppm)=7.45–7.23 (m, 9H, aromatic); 3.60/3.22 (AB, CH$_2$, J$_{AB}$=11.5 Hz); 2.195/1.962 (AB, CH$_2$, J$_{AB}$=11.5 Hz); 1.367 (s, 3H, CH$_3$); 1.067 (s, 3H, CH$_3$);

MS (ES$^+$, 35 V), m/z (% rel. intens.) MH$^+$: 354 (100), 355 (20), 356 (35), 357 (7); (MH—H$_2$O)$^+$: 336 (40), 337 (5), 338 (10), 339 (2).

It was not possible to observe the 2-(4-chlorophenyl)-6,6-dimethyl-1-phenyl-5,6,7,7a-tetrahydro-pyrrolizin-3-one (keto tautomer of 2-(4-chlorophenyl)-6,6-dimethyl-1-phenyl-6,7-dihydro-5H-pyrrolizin-3-ol) expected as a hydrolysis product in any case. After relatively long standing (16 h) of a CHCl$_3$ solution of the product, the 2-(4-chlorophenyl)-6,6-dimethyl-1-phenyl-5,6-dihydropyrrolizin-3-one described in example 29 is obtained as a substance in pure form (H$_2$O elimination).

EXAMPLE 29

2-(4-Chlorophenyl)-6,6-dimethyl-1-phenyl-6,7-dihydropyrrolizin-3-one (Acetoxylation Method According to L. Eberson and L. J önsson, Acta chem. Scand. Ser. B 30, 361 (1976)

6-(4-Chlorophenyl)-2,2-dimethyl-7-phenyl-2,3-dihydro-1H-pyrrolizine (1.6 g, 5 mmol, see above), dipotassium peroxodisulfate (1.62 g, 6 mmol), palladium(II) acetate (0.05 g, 0.2 mmol) and 2,2'-bipyridyl (0.02 g, 0.1 mmol) are suspended in anhydrous acetic acid (20 ml) and stirred at 100° C. for 4 h (note: beforehand, no reaction was to be observed at room temperature after 4 h). The black glacial acetic acid solution is neutralized with Na$_2$CO$_3$ solution (pH 7) and extracted three times with ether (150 ml). The ether solution is washed with NaHCO$_3$ solution, dried over Na$_2$SO$_4$ sicc. and the solvent is removed under reduced pressure. The residue is purified by means of a short column of SiO$_2$ using n-hexane/diisopropyl ether as eluent.

Yield: 88%=1.48 g, C$_{21}$H$_{18}$ClNO, MW=335.84; calc.: C, 75.11%; H, 5.40%; Cl, 10.56%; N, 4.17%; O, 4.76%;

IR (NaCl): 1/λ (cm$^{-1}$)=2956; 1689; 1483; 1379; 1093; 833; 739; 696;

HNMR (CDCl$_3$): δ (ppm)=7.43–7.24 (m, 9H, aromatic); 5.61 (s, 1H, CH); 3.68 (s, 2H, CH$_2$); 1.35 (s, 6H, C(CH$_3$)$_2$);

MS (ES$^+$, 35 V), m/z (% rel. intens.) MH$^+$: 336 (100), 337 (15), 338 (37), 339 (7).

The same substance forms on standing in solution (e.g. CHCl$_3$) from the substance of example no. 28 (see above).

EXAMPLE 30

2-[2-(4-Chlorophenyl)-1-(4-hydroxyphenyl)-6,6-dimethyl-6,7-dihydro-5H-pyrrolizin-3-yl]acetic acid
a) 2-(4-Methoxybenzyl)-4,4-dimethyl-1-pyrroline Magnesium turnings (for Grignard, 48.6 g, 2 mol) are suspended in diethyl ether (480 ml) under argon; 4-methoxybenzyl chloride (31.2 g, 0.2 mol) is dissolved in diethyl ether (200 ml) and 5–10 ml thereof are added to the magnesium. After addition of a crystal of iodine (0.05 g, 0.2 mmol), the reaction mixture is heated without stirring until it becomes cloudy. The remaining 4-methoxy-benzyl chloride solution is rapidly added dropwise with stirring and the batch mixture is then additionally heated under reflux for 1 h. After cooling, the ethereal supernatant is decanted off from the magnesium into a second reaction vessel under an argon protective atmosphere and in the course of this filtered through glass wool.

A solution of 4-chloro-3,3-dimethylbutyronitrile (13.1 g, 0.1 mol) in diethyl ether (60 ml) is added dropwise at room temperature to the Grignard solution thus obtained and, after addition is complete, the solvent (diethyl ether) is distilled off over a distillation bridge up to a bottom temperature of 45–50° C. The residue is made up with anhydrous toluene (450 ml) and the remaining ether is driven off up to a bottom temperature of 90–95° C. After 30 min. at this temp., the reaction mixture is allowed to cool in an ice bath and is decomposed by addition of HCl (10% strength, 200 ml). The HCl acidic phase is separated off in a separating funnel, and the toluene phase is extracted a further 2 times with HCl (10%, 150 ml). The combined HCl extracts are washed with diethyl ether (100 ml) and rendered alkaline (pH 9–10) using conc. ammonia solution (25%). The pyrroline base fraction separating from the water phase is taken up in diethyl ether (2×100 ml), washed with water (2×50 ml) and dried over anhydrous Na$_2$CO$_3$.

After the removal of the solvent in vacuo, 21.7 g of 2-(4-methoxybenzyl)-4,4-dimethyl-1-pyrroline (65% rel. to nitrile employed) remain as a reddish-brown oil, having a purity of 65% (according to gc.).

Yield: 100%=21.7 g, C$_{14}$H$_{19}$NO, MW=217.31; calc.: C, 77.38%; H, 8.81%; N, 6.45%; O, 7.36%;

IR (NaCl): 1/λ (cm$^{-1}$)=2953, 2835, 1511, 1247, 1176, 1035, $^1$HNMR (CDCl$_3$): δ (ppm)=7.15–7.11(AA', 2H, arom.); 6.86–6.82 (BB', 2H, arom.); 3.78 (s, 3H, OCH$_2$); 3.54 (s, 4H, 2CH$_2$); 2.20 (s, 2H, CH$_2$); 1.01 (s, 6H, CH$_3$);

b) 6-(4-Chlorophenyl)-2,2-dimethyl-7-(4-methoxyphenyl)-2,3-dihydro-1H-pyrrolizine With 2-bromo-(4-chlorophenyl)-1-ethanone (15.2 g, 0.065 mol) is introduced in small portions with stirring into the solution of 2-(4-methoxybenzyl)-4,4-dimethyl-1-pyrroline (21.7 g, 65%, 0.065 mol) in MeOH (200 ml). NaHCO, (6.5 g) is then added to the clear solution of the components and the mixture is stirred overnight (16 h). Crystallizate precipitated in the course of this is filtered off (8.6 g), the mother liquor is concentrated in vacuo to a quarter of the starting volume and refrigerated again for crystallization. The recrystallizate (2 g) is combined with the first, and in total 10.6 g (47%) of crystalline 6-(4-chlorophenyl)-2,2-dimethyl-7-(4-methoxyphenyl)-2,3-dihydro-1H-pyrrolizine of melting point XXX° C. are thus obtained.

Yield: 47%=10.6 g, C$_{22}$H$_{22}$ClNO, MW=351.88; calc.: C, 75.10%; H, 6.30%; Cl, 10.06%; N, 3.98%; O, 4.55%;

IR (NaCl): 1/λ (cm$^{-1}$)=cm-1: 2956–2870, 1523, 1504, 1242, 1177, 826, $^1$HNMR (CDCl$_3$): δ (ppm)=ppm: 7.17 (s, 4H, arom.); 7.12–7.05 (AA', 2H, arom.); 6.84–6.78 (BB', 2H, arom.); 6.67 (s, 1H, pyrrole); 3.79 (s, 3H, OCH$_3$); 3.73 (s, 2H, NCH$_2$); 2.76 (s, 2H, CH$_2$); 1.27 (s, 6H, CH$_3$);

c) Ethyl 2-[2-(4-Chlorophenyl)-1-(4-methoxyphenyl)-6,6-dimethyl-6,7-dihydro-5H-pyrrolizin-3-yl]oxoacetate A solution of ethyl oxalyl chloride in THF (20 ml) is added dropwise with stirring in an ice bath to 6-(4-chlorophenyl)-2,2-dimethyl-7-(4-methoxyphenyl)-2,3-dihydro-1H-pyrrolizine (10.6 g, 0.03 mol), dissolved to give a clear solution in THF (100 ml), and the mixture is then stirred for 1 h. The precipitated product (crystallizate a=9.2 g) can be filtered off with suction. The THF solution is evaporated to dryness and the residue is recrystallized from diisopropyl ether (crystallizate b=1.7 g). Together, 10.9 g (80%) of ethyl 2-[2-(4-chlorophenyl)-1-(4-methoxyphenyl)-6,6-dimethyl-5,6-dihydro-5H-pyrrolizin-3-yl]oxoacetate are obtained as crystallizate.

Yield: 80%=10.9 g, $C_{26}H_{26}ClNO_4$, MW=451.95; calc.: C, 69.10%; H, 5.80%; Cl, 7.84%; N, 3.10%; O, 14.16%;

IR (NaCl): 1/λ $(cm^{-1})$=2954–2843, 1739, 1610, 1251, 1250, 1071, 838, $^1$HNMR (CDCl$_3$): δ (ppm)=7.28–7.25 (AA', 2H, arom.); 7.17–7.14 (AA', 2H, arom.); 6.89–6.86 (BB', 2H, arom.); 6.76–6.73 (BB', 2H, arom.); 4.23 (s, 2H, CH$_2$N); 3.75 (s, 3H, OCH$_3$); 3.58 (q, 2H, OCH$_2$); 2.81 (s, 2H, CH$_2$); 1.32 (s, 6H, C(CH$_3$)$_2$); 1.06 (t, 3H, CH$_2$CH$_3$);

d) Ethyl 2-[2-(4-Chlorophenyl)-1-(4-methoxyphenyl)-6,6-dimethyl-6,7-dihydro-5H-pyrrolizin-3-yl]acetate Ethyl 2-[2-(4-chlorophenyl)-1-(4-methoxyphenyl)-6,6-dimethyl-5,6-dihydro-5H-pyrrolizin-3-yl]oxoacetate (4.61 g, 0.010 mmol) is dissolved in abs. CH$_2$Cl$_2$ (60 ml) and zinc(II) iodide (4.46 g, 0.014 mol) is then stirred in. The initially red color of the batch changes to brown. After addition of NaCNBH$_3$ (5.14 g, 0.07 mol), the color of the suspension, which is stirred at room temperature, lightens in the course of the reaction through orange to yellow (5.5 h). After reaction is complete (tlc SiO$_2$/isoether-n-hexane 7:3), water (100 ml) and dil. H$_3$PO$_4$ (8%) are added until the reaction is weakly acidic (pH 5). The CH$_2$Cl$_2$ phase is separated off in a separating funnel and the water phase is extracted with ethyl acetate (3 times 30 ml). The two organic phases are combined, washed with sat. NaCl solution (2 times 50 ml), dried over Na$_2$SO$_4$ sicc. and evaporated to dryness in vacuo. The residue crystallizes from diisopropyl ether (20 ml); 3.0 g (67%) of ethyl 2-[2-(4-chlorophenyl)-1-(4-methoxyphenyl)-6,6-dimethyl-5,6-dihydro-5H-pyrrolizin-3-yl]acetate of melting point 105° C. are obtained.

Yield: 67%=3.0 g, $C_{26}H_{28}ClNO_3$, MW=437.97;

M.p. 105° C.;

IR (NaCl): 1/λ $(cm^{-1})$ 2954–2833, 1725, 1531, 1505, 1292, 1178, 1033, 838;

1HNMR (CDCl$_3$): δ (ppm)=7.26–7.22 (AA', 2H, arom.); 7.14–7.10 (AA', 2H, arom.); 6.99–6.95 (BB', 2H, arom.); 6.76–6.72 (BB', 2H, arom.); 4.18 (q, 2H, CH$_2$); 3.76 (s, 3H, OCH$_3$); 3.74 (s, 2H, CH$_2$); 3.5 (s, 2H, CH$_2$); 2.8 (s, 2H, CH$_2$); 1.31–1.24 (s+t, 9H, C(CH$_3$)$_2$+CH$_2$CH$_3$).

e) Ethyl 2-[2-(4-Chlorophenyl)-1-(4-hydroxyphenyl)-6,6-dimethyl-6,7-dihydro-5H-pyrrolizin-3-yl]acetate Ethyl 2-[2-(4-chlorophenyl)-1-(4-methoxyphenyl)-6,6-dimethyl-5,6-dihydro-5H-pyrrolizin-3-yl]acetate (0.9 g, 2 mmol) is dissolved in CH$_2$Cl$_2$ (20 ml) and cooled to −30° C. At this temperature a solution of BBr$_3$ (0.84 ml, 8.8 mmol) in CH$_2$Cl$_2$ (15 ml) is added through a septum in small portions using a syringe (over 10–15 min.). The internal temperature should not exceed −25° C. here. The mixture is stirred at −30° C. for 3 h (TLC sample: SiO$_2$, n-hexane/ether 7:3, product rf=0.2, starting material rf=0.35), then the reaction is terminated by pouring the cold reaction solution into a semisaturated NaHCO$_3$ solution. The mixture is extracted three times with ethyl acetate (60 ml) and the collected organic phase is washed with sat. NaCl solution (50 ml), dried over Na$_2$SO$_4$ sicc. and the solvent is removed in vacuo. The foaming residue which remains is crystallized from MeOH : 0.54 g (63.7% of theory).

Yield: 63.7%=0.54 g, $C_{25}H_{26}ClNO_3$, MW=423.94;

M.p. ° C.;

IR (NaCl): 1/λ $(cm^{-1})$=3408.3; 3227.0; 2957.6; 2932.2 2869.5; 2901.2; 1732.0; 1713.0; 1531.1; 1506.0; 1262.4; 1214.5; 1172.6; 829.6;

$^1$HNMR (acetone-d6): δ (ppm)=8.1 (OH, phenol.); 7.30–6.64 (m, 8H); 4.15–4.11 (q, 2H, CH$_2$), 3.76 (s, 2H, CH$_2$); 3.52 (s, 2H, CH$_2$); 2.76 (s, 2H, CH$_2$); 1.27 (s, 6H, C(CH$_3$)$_2$), 1.06 (t, 3H, OCH$_2$CH$_3$).

$^{13}$CNMR (acetoned6): δ (ppm)=171.1; 136.3; 133.6; 132.4 131.5; 129.9; 128.7; 128.2; 123.3; 118.5; 115.6 115.1; 61.2; 58.6; 43.7; 40.7; 31.7; 27.7; 14.4.

f) 2-[2-(4-Chlorophenyl)-1-(4-hydroxyphenyl)-6,6-dimethyl-6,7-dihydro-5H-pyrrolizin-3-yl]acetic Acid Ethyl 2-[2-(4-chlorophenyl)-1-(4-hydroxyphenyl)-6,6-dimethyl-5,6-dihydro-5H-pyrrolizin-3-yl]acetate (0.42 g, 1 mmol) is dissolved in a mixture of ethanol (15 ml) and NaOH (3 ml, 10%) under argon and hydrolyzed under reflux for 15 min.

The ethanolic solution is diluted with water (50 ml) and rendered acidic with dil. HCl (10%). The blue-colored solution is extracted with ethyl acetate (3×20 ml), the collected organic phase is washed with sat. NaCl solution (50 ml), dried over Na$_2$SO$_4$ sicc. and the solvent is removed in vacuo. The residue crystallizes from MeOH (5 ml), and 80 mg of crystals (28.6%) are isolated (TLC: SiO2-ether/hexane 2:1).

Yield: 28.6%=0.08 g, $C_{26}H_{28}ClNO_3$, MW=437.97;

M.p. ° C.;

IR (NaCl): 1/λ $(cm^{-1})$=3303.3, 2956.8, 2928.7, 1679.0 1687.0, 1506.1, 1265.1, 1234.2, 827.3.

$^1$HNMR (acetone-d6): δ (ppm)=8.1 (OH, 1H, phenol.); 7.28–6.65 (m, 8H, 2AA'BB' systems), 3.79 (s, 2H, CH$_2$), 3.54 (s, 2H, CH$_2$), 2.77 (s, 2H, CH$_2$), 1.28 (s, 6H, C(CH$_3$)$_2$).

$^{13}$CNMR (acetone-d6): δ (ppm)=172.2, 136.6, 133.7, 132.6, 131.6, 130.0, 128.8, 128.7, 128.4, 123.4, 119.0, 115.7, 115.3, 58.7, 43.8, 40.8, 31.4, 27.9.

EXAMPLE 31

2-[2-(4-Chlorophenyl)-1-(4-methoxyphenyl)-6,6-dimethyl-6,7-dihydro-5H-pyrrolizin-3-yl]acetic Acid A solution of oxalyl chloride (380 mg, 3 mmol) in THF (0.5 ml) is added dropwise with stirring to 6-(4-chlorophenyl)-2,2-dimethyl-7-(4-methoxyphenyl)-2,3-dihydro-1H-pyrrolizine (example 30 b; 0.71 g, 2 mmol), dissolved in tetrahydrofuran (THF) to give a clear solution (5 ml), in an ice bath and the mixture is then stirred for 15 min. Excess oxalyl chloride is decomposed with water (2 ml). After dropwise addition of hydrazine hydrate (1.3 ml, 80%), the mixture is stirred for 30 min., then diethylene glycol (4 ml) is added and the THF contained is distilled off at a bath temperature of 100° C. The residue is cooled to 80° C. and KOH (2.0 g, 35 mmol) is added and the mixture is heated in an oil bath adjusted to a temperature of 160° C. In a water separator, residues of THF, water and the excess of hydrazine pass over, the batch foams, decolorizes and gas is released. The temperature is maintained for 1 h, then the mixture is cooled and diluted with water (20 ml). On acidification with conc. HCl, the free acid precipitates, and is filtered off with suction, washed with water and dried at 60° C.

Yield: 0.65 g (80%), $C_{24}H_{24}ClNO_3$; MW 409.92.

IR (KBr): 1/l $[cm^{-1}]$=2956–2841, 1725, 1709, 1505, 1244, 1177, 1031, 827, $^1$HNMR (acetone-d6): d (ppm)=7.26–7.23 (d, 2H, arom.); 7.14–7.10 (d, 2H, arom.); 6.99–6.95 (d, 2H, arom.);

6.76–6.72 (d, 2H, arom.); 3.74 (s, 3H, OCH$_3$); 3.70 (s, 2H, CH$_2$); 3.57 (s, 2H, CH$_2$); 2.28 (s, 2H, CH$_2$); 1.29 (s; 6H, CH$_3$).

What is claimed:

1. A pyrrolizine compound of the formula I

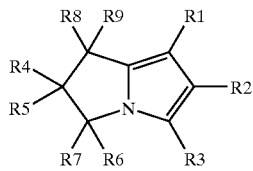

(I)

in which
- R1 and R2, which can be identical or different, are aryl or an aromatic mono- or bicyclic, heterocyclic radical which has 1, 2 or 3 heteroatoms which independently of one another are selected from N, O and S, where the radicals R1 and R2 can optionally be substituted by 1, 2 or 3 groups, which independently of one another are selected from alkyl, halogen, CF$_3$, hydroxy, alkoxy, aryloxy and CN, and can optionally be fused to phenyl or naphthyl;
- R3 is H, alkyl, COOH, COOalkyl, COOAlkphenyl, COCOOH, COCOOalkyl, CHO or A—Y, where
  - A is C$_1$–C$_8$-alkylene or C$_2$–C$_8$-alkenylene, which can optionally be substituted by hydroxyl or alkoxy,
  - Y is COOH, SO$_3$H, OPO(COH)$_2$, OP(OH)$_2$, tetrazolyl, COOalkyl, SO$_3$alkyl, CHO or OH;
  - Alk is C$_1$–C$_4$-alkylene;
- R4, R5, R6 and R7, which can be identical or different, are H, alkyl, hydroxylalkyl or alkoxyalkyl;
- one of the radicals R8 and R9 is H, alkyl, hydroxyalkyl or alkoxyalkyl and the other is hydroxyl, alkoxy or acyloxy or R8 and R9, together with the carbon atom to which they are bonded, are a carbonyl group.

2. A compound of the formula I as claimed in claim 1, where R3 is H, alkyl, COOH, CHO or A—Y, where A is C$_1$–C$_8$-alkylene which is optionally substituted by OH, and Y is COOH, SO$_3$H, OPO(OH)$_2$, CHO or tetrazolyl.

3. A compound of the formula I as claimed in claim 1, where R3 is H, alkyl, COOH, CHO or A—Y, where A is C$_1$–C$_8$-alkylene which is optionally substituted by OH, and Y is COOH.

4. A compound of the formula I as claimed in claim 1, where R1 and R2, which can be identical or different, are aryl or a 5- or 6-membered heterocyclic, aromatic radical, where R1 and R2 independently of one another can contain 1 to 2 halogen, hydroxy, alkoxy and/or CF$_3$ substituents and when the heterocyclic radical can be fused to a phenyl group.

5. A compound of the formula I as claimed in claim 4, where R1 and R2, which can be identical or different, are phenyl, phenyl which is substituted by 1 or 2 halogen atoms or hydroxy groups, thienyl or benzofuranyl.

6. A compound of the formula I as claimed in claim 4, where R1 is phenyl and R2 is monohalo- or monohydroxy-substituted phenyl or benzofuranyl.

7. A compound of the formula I as claimed in claim 1, where R4 is hydroxyalkyl, R5 is H or alkyl and R6 and R7 independently of one another are or alkyl.

8. A compound of the formula I as claimed in claim 1, where R8 and R9, together with the carbon atom to which they are bonded, are a carbonyl group.

9. A pharmaceutical composition, comprising at least one compound as claimed in claim 1, if appropriate together with pharmaceutically acceptable vehicles and/or additives.

10. 2-[2-(4-Chlorophenyl)-6-hydroxymethyl-6-methyl-1-phenyl-6,7-dihydro-5H-pyrrolizin-3-yl]acetic acid.

11. 2-[2-(4-Chlorophenyl)-1-(4-hydroxyphenyl)-6,6-dimethyl-6,7-dihydro-5H-pyrrolizin-3yl]acetic acid.

* * * * *